United States Patent
Scadden et al.

(10) Patent No.: US 7,462,483 B2
(45) Date of Patent: Dec. 9, 2008

(54) P27 AND P21 IN GENE THERAPIES

(75) Inventors: David T. Scadden, Weston, MA (US); Tao Cheng, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/803,687

(22) Filed: Mar. 9, 2001

(65) Prior Publication Data

US 2002/0006663 A1  Jan. 17, 2002

Related U.S. Application Data

(60) Provisional application No. 60/213,627, filed on Jun. 23, 2000, provisional application No. 60/188,120, filed on Mar. 9, 2000.

(51) Int. Cl.
*C12N 5/08* (2006.01)
(52) U.S. Cl. .................. 435/372; 435/373; 435/377
(58) Field of Classification Search .............. 435/455, 435/366
See application file for complete search history.

(56) References Cited

U.S. PATENT DOCUMENTS

| | | | |
|---|---|---|---|
| 5,176,996 A | 1/1993 | Hogan et al. | |
| 5,256,775 A | 10/1993 | Froehler | |
| 5,264,564 A | 11/1993 | Matteucci | |
| 5,958,769 A | * 9/1999 | Roberts et al. | ............... 435/375 |

FOREIGN PATENT DOCUMENTS

| | | |
|---|---|---|
| WO | WO 97/26327 | 7/1997 |
| WO | WO 97/38091 | 10/1997 |

OTHER PUBLICATIONS

Waldman et al. p21 is necessary for the p53 mediated G-1 arrest in human cancer cells Cancer Research vol. 55 1995 (previously cited).*
Branch A good antisense is hard to find. TIBS vol. 23 pp. 45-50 1998.*
Cheng Oncogene (2004) 7256-7266.*
Stojkovic et al. Reproduction (Sep. 2004) 128(93) 259-67.*
Zhu et al. Current Drug Targets (Feb. 2005) 6(1) 97-110.*
Czyz et al. Biol. Chem., vol. 384, pp. 1391-1409 2003.*
Waldman, et al., "p21 Is Necessary for the p53-Mediated $G_1$ Arrest in Human Cancer Cells", *Cancer Research*, 55: 5187-5190, 1995.
International Search Report issued for corresponding PCT application PCT/US01/07538.
Asiedu, et al., Complex Regulation of CDK2 During Phorbol Ester-Induced Hematopoletic Differentiation, *Blood*, 90: 3430-3437, 1997.
Becker, et al., "Adhesion Receptor Expression by Hematopoietic Cell Lines and Murine Progenltors: Modulation by Cytokines and Cell Cycle Status", *Exp. Hematal*, 27: 533-541, 1999.
Berardi, et al., "Functional Isolation and Characterization of Human Hematopoictic Stem Cells", *Science*, 267: 104-108, 1995.
Braun, et al., "A Positive Effect of $p21^{cip1/waf1}$ in the Colony Formation from Murine Myeloid Progenitor Cells as Assessed by Retroviral-Mediated Gene Transfer" *Blood Cells Mol. Dis.* 24: 138-148, 1998.
Brugarolas, et al., "Radiation-Induced Cell Cycle Arrest Compromised by p21 Deficiency" *Nature*, 377: 552-557, 1995.
Carver-Moore, et al., "Low Levels of Erythroid and Myeloid Progenitors in Thromboppoietin- and c-mpl-deficient mice", *Blood*, 88: 803-808, 1996.
Chan, et al., "Triplex DNA: Fundamentals, Advances, and Potential Applications for Gene Therapy" *J. Mol. Med.*, 75(4): 267-282, 1997.
Cheng, et al., Hematopoictic Stem Cell Qulescence Maintained by p21(cip1/waf1), *Science*, 287: 1804-1808, 2000.
Cheng, et al., "Temporal Mapping of Gene Expression Levels During the Differentiation of Individual Primary Hematopoietic Cells", *Proc. Natl. Acad. Sci. USA*, 93, 13158-13163, 1996.
Coats, et al., "Requirement of p27Kip1 for Restriction Point Control of the Fibroblast Cell Cycle". *Science*: 272: 877-880, 1996.
Crooke, "Molecular Mechanisms of Action of Antisense Drugs", *Biochim. Biophys. Acta*, 1489(1): 31-44, 1999.
Cunto, et al., "Inhibitory Function of $p21^{Cip1/WAF1}$ in Differentiation of Primary Mouse Keratinocytes Independent of Cell Cylce Control", *Science*, 280:1069, 1998.
Dao, et al., "Reduction in Levels of the Cyclin-Dependent Kinase Inhibitor p27(kip-1) Coupled with Transforming Growth Factor Beta Neutralization Induces Cell-Cycle Entry and Increases Retroviral Transduction of Primitive Human Hematopoietic Cells" *Proc. Natl. Acad. Sci. USA*, 95: 13006-13011, 1998.

(Continued)

*Primary Examiner*—James S Ketter
(74) *Attorney, Agent, or Firm*—Choate, Hall & Stewart, LLP; C. Hunter Baker

(57) ABSTRACT

The expansion of a population of stem cells or progenitor cells, or precursors thereof, may be accomplished by disrupting or inhibiting $p21^{cip1/waf1}$ and/or p27, cyclin dependent kinase inhibitors. In the absence of p27 activity, progenitor cells move into the cell cycle and proliferate; whereas in the absence of p21 activity, stem cells move into the cell cycle and proliferate without losing their pluripotentiality (i.e., their ability to differentiate into the various cell lines found in the blood stream). Any type of stem cell or progenitor cell, or precursor thereof, including, but not limited to, hematopoietic, gastrointestinal, lung, neural, skin, muscle, cardiac muscle, renal, mesenchymal, embryonic, fetal, or liver cell may be used in accordance with the invention. The present invention provides a method of expanding a cell population, cells with decreased p27 and/or p21 activity, transgenic animals with a disrupted p27 and/or p21 gene, pharmaceutical compositions comprising the cells of the invention, and methods of using these cells in gene therapy (e.g., stem cell gene therapy) and bone marrow transplantation.

23 Claims, 21 Drawing Sheets

OTHER PUBLICATIONS

Deng, et al., "Mice Lacking p21 $^{Cip1/WAF1}$ Undergo Normal Development, But Are Defective in G1 Checkpoint Control" *Cell*, 82: 675-684, 1995.

Drize, et al., "Local Clonal Analysis of the Hematopoietic System Shows That Multiple Small Short-Living Clones Maintain Life-Long Hematopoiesis in Reconstituted Mice" *Blood*, 88: 2927-2938, 1996.

Durand, et al., p27kip1 Alters the Response of Cells to Miltogen and is Part of a Cell-Intrinsic Timer that Arrests the Cell Cycle and Initiates Differentiation:, *Curr. Biol.* 8: 431-440, 1998.

Fadok, et al., Exposure of Phosphatidylscrine on the Surface of Apoptotic Lymphocytes Triggers Specific Recognition and Removal by Macrophages, *J. Immunol.* 148: 2207-2216, 1992.

Fero, et al., A Syndrome of Multiorgan Hyperplasia with Features of Glgantism Tumorlgenesis, and Female Sterility in p27 (kip1)-Deficient Mice Cell 85:733-744, 1996.

Gardner, et al., "Hematopoictic Precursor Cell Exhaustion in a Cause of Proliferative Defect in Primitive Stem Cells (PHSC) After Chemotherapy. Exp. Hermatol." Exp. Hermatol, 25: 495-501, 1997.

Gothot, et al., "Functional Heterogeneity of Human CD34(+) Cells Isolated in Subcompartments of the G0/G1 Phase of the Cell Cycle", *Blood*, 90: 4384-4393, 1997.

Gothot, et al., Assessment of Proliferative and Colony-Forming Capacity After Successive in Vitro Divisions of Single Human $CD34^+$ Cells Initially Isolated in $G_0$ *Exp. Hermatol.* 26: 562, 1998.

Grzegorzewski, et al., "Recombinant Transforming Growth Factor Beta 1 and Beta 2 Protect Mice From acutely Lethal Doses of 5-Fluorouracil and Doxorubicin", *J. Exp. Med.* 180: 1047-1057, 1994.

Harrison, et al., "Loss of Proliferative Capacity in Immunohemopoietic Stem Cells Caused by Serial Transplantation Rather Than Aging", *J. Exp. Med.* 147: 1526-1531, 1978.

Harrison, D.E., Competitive Repopulation: A New Assay For Long-Term Stem Cell Functional Capacity, *Blood*, 55: 77-81, 1980.

Harrison, et al., Loss of Stem Cell Repopulating Ability Upon Transplantation, *J. Exp. Med.* 156: 1767-1779, 1982.

Hengst, et al., "Translational Control of p27Kip1 Accumulation During the Cell Cycle," *Science*, 271: 1861-1864, 1996.

Holyoake, "Isolation of a Highly Quiescent Subpopulation of Primitive Leukkemic Cells in Chronic Myeloid Leukemia" et al., *Blood*, 94: 2056-2064, 1999.

Kiyokawa, et al., Enhanced Growth of Mice Lacking the Cyclin-Dependent Kinase Inhibitor Function of p27(Kip1). *Cells*, 85, 721-732, 1996.

Kranenburg, et al., "Inhibition of Cyclin-Dependent Kinase Activity Triggers Neuronal Differentiation of Mouse Neuroblastoma Cells", *J. Cell Biol.* 131: 227-234, 1995.

LaBaer, et al., "New Functional Activities for the p21 Family of CDK Inhibitors", *Genes Dev.* 11: 847-862, 1997.

Leemhuis, et al., "Isolation of Primitive Human Bone Marrow Hematopoietic Progenitor Cells Using Hoechst 33342 and Rhodamine 123", *Exp. Hematol.* 24: 1215-1224, 1996.

Lerner, et al., "5-Fluorouracil Spares Hematopoietic Stem Cells Responsible for Long-Term Repopulation" *Exp. Hematol.* 18: 114-118, 1990.

Liu, et al., Transcriptional Activation of the Human p21 (WAF1/CIP1) Gene by Retinoic Acid Receptor. Correlation with Retinoid Induction of U937 Cell Differentiation. *J. Biol. Chem.* 271(49): 31723-31728, 1996.

Mantel, et al., Involvement of p21cip1 and p27kip-1 in the Molecular Mechanisms of Steel Factor-Induced Proliferative Synergy in Vitro and of p21cip in the Maintenance of Stem/Progenitor Cells in Vivo. *Blood*, 88: 3710-3719, 1996.

Mauch, et al., Hematopoictic Stem Cell Compartment: Acute and Late Effects of Radiation Therapy and Chemotherapy, *Int. J. Radiat. Oncol. Biol. Phys.* 31: 1319-1339, 1995.

Müller, et al., "Genetic Control of the Frequency of Hematopoietic Stem Cells in Mice: Mapping of a Candidate Locus to Chromosome1" *J. Exp. Med.* 183: 1141-1150, 1996.

Müller, et al., "ES Cells Have Only a Limited Lymphopoietic Potential After Adoptive Transfer into Mouse Recipients", *Development*, 118: 1343-1351, 1993.

Nakayama, et al., Mice Lacking p27(Kip1) Display Increased Body Size, Multiple Organ Hyperplasia, Retinal Dysplasia, and Pituitary Tumors, *Cell*, 85: 707-720, 1996.

Nakanishi, et al., "Exit from $G_0$ and Entry into the Cell Cycle of Cells Expressing $P21^{Sdi1}$ Antisense RNA" *Proc. Natl. Acad. Sci., USA*, 92: 4352-4356, 1995.

Ogawa, M., "Differentiation and Proliferation of Hematopoietic Stem Cells", *Blood*, 81: 2844-2853, 1993.

Pagano, et al., Role of the Ubiquitin-Proteasome Pathway in Regulating Abundance of the Cyclin-Dependent Kinase Inhibitor p27 (see comments) *Science*, 269: 682-685, 1995.

Ploemacher, et al., Use of Limiting-dilution Type Long-Term Marrow Cultures in Frequency Analysis of Marrow-Repopulation and Spleen Colony-Forming Hematopletic Stem Cells in the Mouse. *Blood*, 78: 2527-2533, 1991.

Ploemacher, et al., "An In Vitro Limiting-Dilution Assay of Long-Term Repopulating Hematopoietic Stem Cells in the Mouse" *Blood*, 74(8): 2755-2763, 1989.

Polyak, et al., "p27kip1, A Cyclin-Cdk Inhibitor, Links Transforming Growth Factor-Beta and Contact Inhibition to Cell Cycle Arrest." *Genes Dev.* 8: 9-22, 1994.

Rivard, et al., Abrogation of p27Kip1 by cDNA Antisense Suppresses Quiescence (GO State) in Fibroblasts, *J. Biol. Chem.* 271: 18337-18341, 1996.

Roy, et al., Expression and Function of Cell Adhesion Molecules on Fetal Liver, Cord Blood and Bone Marrow Hematopoletic Progenitors; Implications for Anatomical Localization and Developmental Stage Specific Regulation of Hematopoiesis, *Exp. Mematol.* 27: 302-312, 1999.

Schwarze, et al., "In Vivo Protein Transduction: Delivery of a Biologically Active Protein into the Mouse" *Science*, 285: 1569-1572, 1999.

Sherr, "G1 Phase Progression: Cycling on Cue" *Cell*, 79: 551-555, 1994.

Sherr, et al., Inhibitors of Mammalian G1 Cyclin-Dependent Kinases. *Genes Dev.* 9: 1149-1163, 1995.

Sherr, C.J., "Cancer Cell Cycles" *Science*, 274: 1672-1677, 1996.

Shivdassani, et al., "The Transcriptional Control of Hematopoiesis", *Blood*, 87: 4025-4039, 1996.

Shull, et al., "Targeted Disruption of the Mouse Transforming Growth Factor-Beta 1 Gene Results in Multilocal Inflammatory Disease", *Nature*, 359: 693-699, 1992.

Spangrude, et al., "Purification and Characterization of Mouse Hematopoietic Stem Cells" *Science*, 241: 58-62, 1988.

Szilvassy, et al., "Quantitative Assay to Totlpotent Reconstituting Hematopoietic Stem Cells by a Competitive Repopulation Strategy", *Proc. Natl. Acad. Sci. USA*, 87: 8736-8740, 1990.

Taniguchi, et al., "Expression of p21 (Cip1/Waf1/Sdi1) and $p27^{Kip1}$ Cyclin-Dependent Kinase Inhibitors During Human Hematopoiesis", *Blood*, 93: 4167-4178, 1999.

Tenen, et al., "Transcription Factors, Normal Myeloid Development, and Leukemia", *Blood*, 90:489-519, 1997.

Testa, et al., "Expression of Growth Factor Receptors in Unilineage Differentiation Culture of Purified Hematopoletic Progenitors," *Blood*, 88: 3391-3406, 1996.

Uchida, "Rapid and Sustained Hematopoietic Recovery in Lethally Mice Transplanted with Purified $Thy-1.^{lo}$ $Lin-Sca-1^+$ Hematopoietic Stem Cells" et al., *Blood*, 83: 3758, 1994.

Wang, et al., "Resistance to Apoptosis Conferred by Cdk Inhibitors During Myocyte Differentiation" *Science*, 273: 359, 1996.

Weston, et al., "New Fluorescent Dyes for Lymphocyte Migration Studies Analysis by Flow Cytometry and Fluorescence Microscopy", *J. Immunol. Methods*, 133: 87-97, 1990.

Wolf, et al., "In Vivo and In Vitro Characterization of Long-Term Repopulating Primitive Hematopoietic Cells Isolated by Sequential Hoechst 33342-Rhodamine 123 FACS Selection" *Exp. Hematol.* 21: 614-622, 1993.

Yaroslavsky, et al., "Subcellular and Cell-Cycle Expression Profiles of CDK-Inhibitors in Normal Differenting Myeloid Cells", *Blood*, 93: 2907-2917, 1999.

Zijlmans et al., "Telomeres in the Mouse Have Large Inter-Chromosomal Variations in the Number of $T_2 AG_3$ Repeats" *Proc. Natl. Acad. Sci. USA*, 94: 7423, 1997.

Cheng, et al., "Stem Cell Repopulation Efficiency But Not Pool Size Governed by $p27^{kip1}$" *Nature Medicine*, 6(11): 1235-1240, 2000.

Eppich, et al., "Pulsed Electric Fields for Selection of Hematopoietic Cells and Depletion of Tumor Cell Contaminants", *Nature Biotechnology*, 18: 882-887, 2000.

Cheng, et al., "Stem Cell Repopulation Efficiency but Not Pool Size is Governed by $p27^{kip1}$", *Nature Medicine*, 6(11): 1235-1240, 2000.

Qiu, et al., "Regenerative Response in Ischemic Brain Restricted by $p21^{cip1/waf1}$" *J. Exp. Med.*, 199(7): 937-945, 2004.

Yuan, et al., "In Vivo Self-Renewing Divisions of Haematopoietic Stem Cells are Increased in the Absence of the Early G1-Phase Inhibitor, $p18^{INK4C}$", *Nature Cell Biology*, 6(5): 436-442, 2004.

Zhang, et al., "Transient Reduction of $p21^{Waf1/Cip1/Sdi1}$ by RNAi Increases the Relative Number and Gene Transduction Efficiency of Human Hematopoietic Stem Cells," unpublished manuscript.

Clarke, "Isolation and characterization of human mammary stem cells," *Cell Prolif.* 38: 375-386, 2005.

Kippin et al., "p21 loss compromises the relative quiescence of forebrain stem cell proliferation leading to exhaustion of their proliferation capacity," *Genes & Development*, 19: 756-767, 2005.

Qiu et al., "Regenerative Response in Ischemic Brain Restricted by $p21^{cip1/waf1}$," *J. Exp. Med.*, 199(7): 937-945, Apr. 15, 2004.

Topley, et al., "$p21^{WAF1/cip1}$ functions as a suppressor of malignant skin tumor formation and a determinant of keratinocyte stem-cell potential," *Proc. Natl. Acad. Sci. USA*, 96: 9089-9094, Aug. 1999.

\* cited by examiner

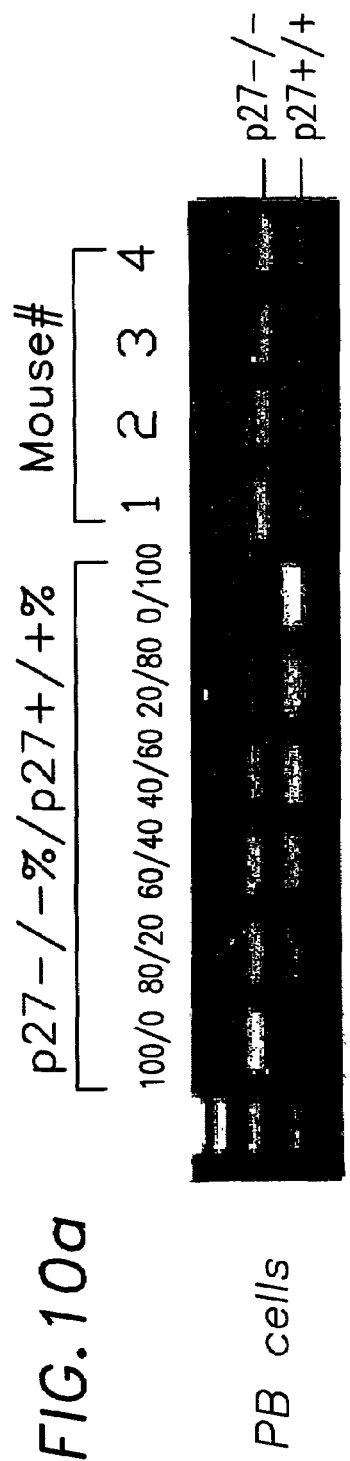
FIG. 10a  PB cells
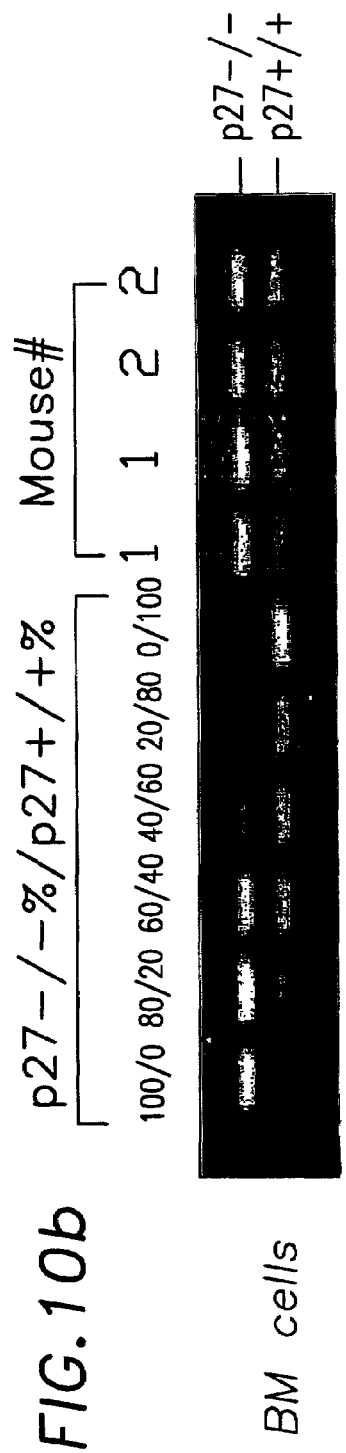
FIG. 10b  BM cells

CFU-mix colonies of transduced progenitor cells

Total colony number of transduced progenitor cells

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:Genomic DNA
      was isolated from tail biopsy and analyzed by
      amplification using three primers: p21 + 116F

<400> SEQUENCE: 1
aagccttgat tctgatgtgg gc                                              22

<210> SEQ ID NO 2
<211> LENGTH: 22
<212> TYPE: DNA

```
<213> ORGANISM: Artificial Sequence
<220> FEATURE:
<223> OTHER INFORMATION: Description of Artificial Sequence:Genomic DNA
      was isolated from tail biopsy and analyzed by
      amplification using three primers: p21 + 116F

<400> SEQUENCE: 2
tgacgaagtc aaagttccac cg                                            22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Genomic DNA
      was isolated from tail biopsy and analyzed by
      amplification using three primers: p21 + 116F

<400> SEQUENCE: 3
gctatcagga catagcgttg gc                                            22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Sry primer.

<400> SEQUENCE: 4
tcatgagact gccaaccaca g                                             21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Sry primer.

<400> SEQUENCE: 5
catgaccacc accaccacca ccaa                                          24

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Myogenin
      primer.

<400> SEQUENCE: 6
ttacgtccat cgtggacagc                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Myogenin
      primer.

<400> SEQUENCE: 7
tgggctgggt gttagtctta                                               20

<210> SEQ ID NO 8
<211> LENGTH: 23
<212> TYPE: DNA
<213> ORGANISM: Artificial Sequence
```

```
<220> FEATURE:
<223> OTHER INFORMATION: Description of Artificial Sequence:Genomic DNA
      was isolated from tail biopsy and analyzed by
      amplification using three primers.

<400> SEQUENCE: 8
tcaaacgtga gagtgtctaa cgg                                           23

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Genomic DNA
      was isolated from tail biopsy and analyzed by
      amplification using three primers.

<400> SEQUENCE: 9
acgggcttat gattctgaaa gtcg                                          24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:Genomic DNA
      was isolated from tail biopsy and analyzed by
      amplification using three primers.

<400> SEQUENCE: 10
atattgctga agagcttggc gg                                            22
```

P27 AND P21 IN GENE THERAPIES

RELATIONED APPLICATIONS

The present application claims priority to co-pending provisional applications, U.S. Ser. No. 60/213,627, filed Jun. 23, 2000, and U.S. Ser. No. 60/188,120, filed Mar. 9, 2000, each of which is incorporated herein by reference in its entirety.

GOVERNMENT SUPPORT

The work described herein was supported, in part, by grants from the National Institutes of Health (DK50234, HL44851, HL55718, DK02761, AI07387) and the U.S. Department of Defense. The United States government may have certain rights in the invention.

BACKGROUND OF THE INVENTION

Hematopoiesis is the process by which hematopoietic pluripotent stem cells mature into functional blood cells (i.e., red blood cells (erythrocytes), white blood cells (T-cells, B-cells, NK cells, dendritic cells, basophils, polymorphonucleated cells, macrophages, monocytes, and eosinophils), and platelets). In the current model of hematopoiesis, all blood cells begin as pluripotent stem cells. These pluripotent cells are partitioned between resting and proliferating compartments, and during hematopoiesis some of these cells are transformed to committed progenitors of red blood cells, white blood cells, or platelets by the influence of multiple growth factors and cytokines. These committed progenitor cells undergo further differentiation and commitment influenced by growth factors and cytokines. The committed cells are also partitioned between resting and proliferating compartments; however, many more of these cells are proliferating. These committed progenitor cells give rise to morphologically identifiable immature precursor cells (i.e., blasts), which populate the marrow. These precursor cells mature further and eventually enter the blood where they are influenced further by growth factors and cytokines.

High levels of production of mature blood cells are needed to replace their rapid turnover in the body (tens of billions of cells per day in the human with rapid increments during times of physiologic stress). Maintenance of blood cell production requires a highly cytokine responsive progenitor cell pool with prodigious proliferative capacity and a smaller population of stem cells intermittently feeding daughter cells into the proliferative compartment. The proliferative activity of these very important hematopoietic stem cells has been hypothesized to be highly restricted to prevent susceptibility to myelotoxic insult or consumption of the regenerative cell pool (Mauch et al. *Bone Marrow Transplant* 4:601-607, 1989; Mauch et al. *Int. J Radiat. Oncol. Biol Phys.* 31:1319-39, 1995; Gardner et al. *Exp. Hematol.* 25:495-501, 1997; each of which is incorporated herein by reference). Once these stem cells embark on a path of high proliferation, they appear to survive only 1 to 3 months (Drize et al. *Blood* 88:2927-2938, 1996; incorporated herein by reference). Hematopoietic tissue has therefore been thought to be organized such that stem cells are relatively quiescent and cytokine resistant, but that their more differentiated offspring have extremely robust proliferative potential (Ogawa *Blood* 81:2844-53, 1993; incorporated herein by reference). The dichotomy of resistance to proliferative signals by stem cells and the brisk responsiveness by progenitor cells is a central feature of hematopoiesis, and the molecular mechanisms governing it are not well understood.

Stem cells and progenitor cells are used in research, bone marrow transplantation, and gene therapy; however, stem cell expansion without loss of multipotentiality is a problem. Current technology is based on driving stem cells to proliferate with superphysiologic doses of cytokines. These cytokines unfortunately have pleiotropic effects which include differentiation of primitive cells. The result of these techniques is expanded cell numbers but a loss of multipotentiality. Due to these problems in expanding stem cell populations, one third of patients are currently denied autologous bone marrow transplantation because of inadequate stem cell numbers. For example, cord blood stem cells are the best source of stem cells for minority groups, yet they are inadequate in number to transplant adults.

Stem cell gene therapy has been a failure to date largely due to the inability to achieve gene transfer in quiescent cells. Both bone marrow transplantation and gene therapy would be revolutionized by successful stem cell and progenitor cell expansion technology.

SUMMARY OF THE INVENTION

The present invention provides a method of expanding a population of stem cells or progenitor cells by inhibiting p27 and/or p21 activity in the cells. The method comprises steps of providing at least one cell, in which the activity and/or amount of p27 and/or p21 within the cell is decreased, and expanding the population of cells. Although cells of any origin or at any stage of differentiation may be used, hematopoietic stem or progenitor cells are preferred. Inhibition of p27 and/or p21 may be accomplished by disruption of the gene encoding p27 and/or p21, inhibition of gene transcription, inhibition of translation of the p27 and/or p21 mRNA, inhibition the kinase inhibiting activity of the p27 and/or p21 protein, inhibition of the exogenous signals upregulating p27 and/or p21, inhibition of signaling pathways controlling p27 and/or p21 expression, etc. The present invention demonstrates that a decrease in p27 activity in the progenitor cells disrupts the dominant anti-proliferative tone that governs cell cycle entry by progenitor cells and induces cell proliferation. Similarly, the invention shows that a decrease in p21 activity in the stem cells disrupts the dominant anti-proliferative tone that governs cell cycle entry by stem cells and permits expansion of the stem cells without differentiation or with minimal differentiation or without loss of multipotentiality. Disrupting and/or inhibiting p27 and/or p21 allows for a highly specific and highly feasible strategy for permitting stem and/or progenitor cell expansion leading to the use of these cells in bone marrow transplants, gene therapy, or regeneration of other tissue types by pluripotent progenitor cells.

The present invention also provides a population of progenitor cells or stem cells containing a disrupted or inhibited p27 and/or p21. These cells may have decreased p27 and/or p21 activity when compared to wild type cells, or the inhibition of p27 and/or p21 activity may have only been temporarily induced in order to expand the population and the cells may "re-gain" full p27 activity after the expansion. In certain embodiments, the p27 and/or p21 gene may be disrupted in these cells—both copies or only one copy. The p27 and/or p21 gene may be disrupted in the progenitor cell itself or in a precursor of the progenitor cell (e.g., a stem cell). The present invention also provides a pharmaceutical composition comprising a therapeutically effective amount of p27-depleted progenitor cells or precursors thereof, and an optional pharmaceutically acceptable excipient. In certain preferred embodiments, the inventive p27-depleted progenitor cells, or precursors thereof, are also depleted for p21. The present invention also provides a pharmaceutical composition comprising a therapeutically effective amount of p21-depleted stem cells or progenitor cells, and an optional pharmaceutically acceptable excipient. In certain preferred embodiments, the iventive p21-depleted stem cells, or derivative thereof, are also depleted of p27.

The present invention also provides a transgenic animal with at least one copy of the p21 and/or p27 genes altered. The genes may be altered in all cells of the animal or in only a portion of the cells of the animal. In a preferred embodiment, the hematopoietic cells of the animal have had at least one copy of the p21 and p27 genes altered.

In another aspect of the present invention, the cells of the invention are used in bone marrow transplantation. In certain preferred embodiments, the genome of at least one cell has been altered by the hands of man, and these cells are optionally delivered to an animal or plant. In another preferred embodiment, cells in which the p21 activity, p27 activity, or both activities are decreased are administered to an animal or plant.

In yet another aspect of the present invention, the cells of the invention are used in gene therapy (e.g., stem cell gene therapy) or tissue regeneration. In a preferred embodiment, the p21 and/or p27 gene is altered in the administered cells. In another particularly preferred embodiment, the p21 and/or p27 activity is decreased compared to a wild type cell. The genome of at least one cell may also be altered by the hands of man to correct a genetic defect, and these altered cells are optionally delivered to an animal or plant. The genomic alteration within these cells may be accomplished before, after, or during the expansion of the cell population. The genomic alteration may include, but is not limited to, insertion of an exogenous gene, mutation of an endogenous gene, repair of an endogenous gene, deletion of a gene, etc.

BRIEF DESCRIPTION OF THE DRAWING

FIG. 14 demonstrates the percent of human cells detectable in the blood of animals transplanted with cells exposed to either control (GFP-V) or p21-anti-sense encoding (p21-AS-V) vector.

Definitions

Figure 1A:
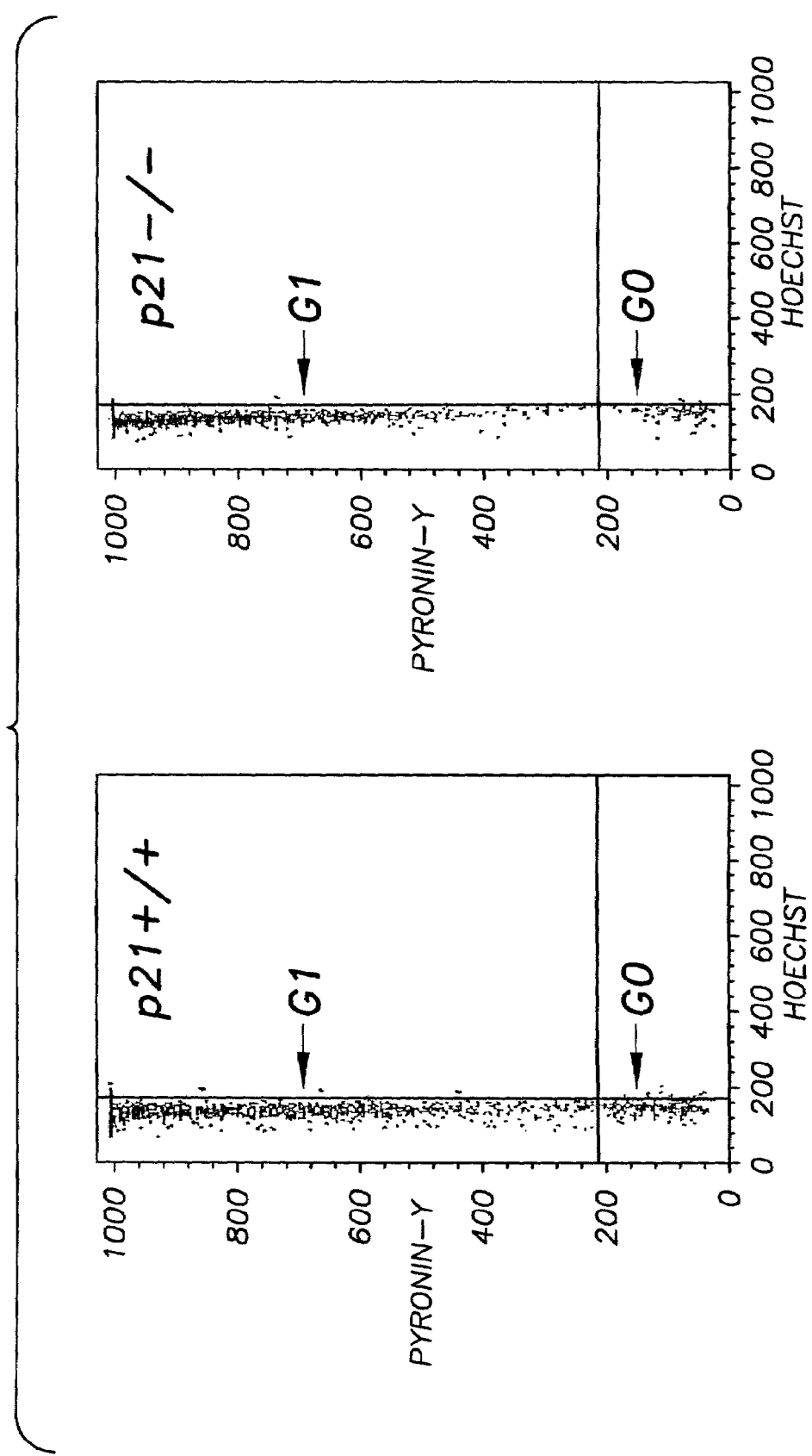
FIG. 1. Distribution of $G_0$ vs. $G_1$ in the lineage negative bone marrow mononuclear cell population defines an increased cycling fraction in p21 −/− mice. Mouse bone marrow cells were stained with lineage antibodies, pyronin Y (RNA dye), and Hoechst 33342 (DNA dye). Lineage negative (Lin) cells were gated using a stringent parameter. Cells residing in $G_0$ appear at the bottom of the $G_0/G_1$ peak and $G_1$ cells are the upper part as indicated (a). The average $G_0$% in lin-Hoechst$^{low}$ cells from six experiments is shown in the graph (b). Data represent the Mean+SE, n=6, p=0.005. 1-2 litter mates of each genotype were analyzed in each experiment.
Figure 1B:
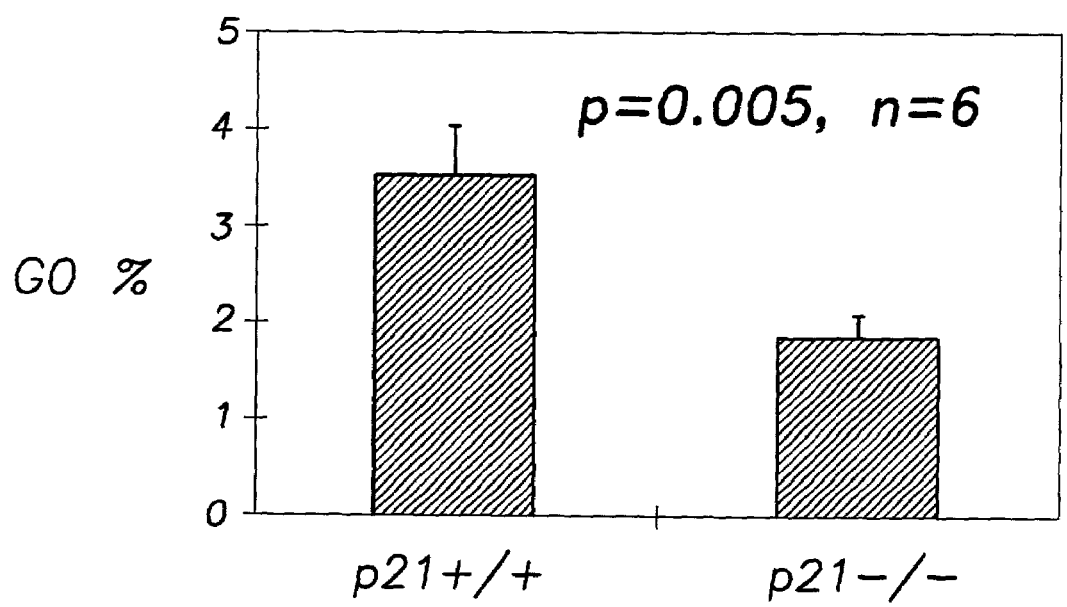

"Animal": The term animal, as used herein, refers to human as well as non-human animals, including, for example, mammals, birds, reptiles, amphibians, and fish. Preferably, the animal is a mammal (e.g., a rodent, a mouse, a rat, a rabbit, a monkey, a dog, a cat, or a pig), most preferably a human. An animal may be a transgenic animal.

"Decreased p21 activity": The phrase "decreased p21 activity" refers to a decreased amount of p21 protein or mRNA transcript in the cell and/or a decreased level of p21 activity. The decreased p21 activity may be accomplished by any method known in the art including small molecule inhibitors of p21, antisense agents, aptamers, gene knockout, antibodies, overabundance of the countervailing cyclin D/CDK4 complex to overwhelm p21 inhibition, etc. Preferably, the reduction in activity is at least 50% when compared to wild type cells. More preferably, the reduction is at least 75% or 90%, and most preferably, decreased p21 activity refers to an undetectable level of p21 activity.

"Decreased p27 activity": The phrase "decreased p27 activity" refers to a decreased amount of p27 protein or MRNA transcript in the cell and/or a decreased level of p27 activity. The decreased p27 activity may be accomplished by any method known in the art including small molecule inhibitors of p27, antisense agents, aptamers, gene knockout, antibodies, overabundance of the countervailing cyclin E/CDK2 and/or cyclin A/CDK2 complexes to overwhelm p27 inhibition, etc. Preferably, the reduction in activity is at least 50% when compared to wild type cells. More preferably, the reduction is at least 75% or 90%, and most preferably, decreased p27 activity refers to an undetectable level of p27 activity (e.g., by Northern analysis, Western analysis, enzymatic assay, etc.).

"Homologous" or "homologue": The term "homologous", as used herein is an art-understood term that refers to nucleic acids or polypeptides that are highly related at the level of nucleotide or amino acid sequence. Nucleic acids or polypeptides that are homologous to each other are termed "homologues."

The term "homologous" necessarily refers to a comparison between two sequences. In accordance with the invention, two nucleotide sequences are considered to be homologous if the polypeptides they encode are at least about 50-60% identical, preferably about 70% identical, for at least one stretch of at least 20 amino acids. Preferably, homologous nucleotide sequences are also characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids.

"Peptide" or "Protein": According to the present invention, a "peptide" or "protein" comprises a string of at least three amino acids linked together by peptide bonds. Inventive peptides preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive peptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polynucleotide" or "oligonucleotide": Polynucleotide or oligonucleotide refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-amninoadenosine, 2-thiothymidine, inosine, pyrrolo-pyrimidine, 3-methyladenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-hydroxylribose, 2'-fluororibose, ribose, 2'-deoxyribose, and hexose), or modified phosphate groups (e.g., phosphorothioates and 5'-N-phosphoramidite linkages).

"Progenitor cell": "Progenitor cell" refers to unipotent or multipotent, committed or determined cells derived from stem cells. Progenitor cells undergo further differentiation and commitment to give rise to morphologically identifiable immature cells. Progenitor cells which may be used in accordance with the present invention include hematopoietic, neural, mesenchymal, gastrointestinal, muscle, cardiac muscle, kidney, skin, lung, and embryonic progenitor cells. In certain preferred embodiments, hematopoietic progenitor cells are positive for the CD34 marker. In another preferred embodiment, hematopoietic progenitor cells are positive for Sca-1 and lineage markers (Spangrude et al. "Purification and characterization of mouse hematopoietic stems cells [published erratum appears in *Science* 1989 June 2;244 (4908): 1030]" *Science* 241:58-62, 1988; incorporated herein by reference). Progenitor cells may be identified morphologically, kinetically, or operationally as further described below in the definition of a stem cell.

"Stem cell": "Stem cell" refers to any pluripotent cell that under the proper conditions will give rise to a more differentiated cell. Stem cells which may be used in accordance with the present invention include hematopoietic, neural, mesenchymal, gastrointestinal, muscle, cardiac muscle, kidney, skin, lung, and embryonic stem cells. To give but one example, a hematopoietic stem cell can give rise to differentiated blood cells (i.e., red blood cell (erythrocyte), white blood cell (T-cell, B-cell, neutrophil, basophil, eosinophil, monocyte, macrophage), or platelet) or neural or muscle cells. In terms of morphology, hematopoietic stem cells are small mononuclear cells normally found in the bone marrow of adults. These cells can be mobile and can also be found in the blood at a concentration of 1-5 per $10^5$ nucleated cells. During development, hematopoietic stem cells may be found in various locations in the body including the liver, spleen, thymus, lymph nodes, yolk sac, blood islands, and bone marrow.

Stem cells can also be characterized by their ability (1) to be self-renewing and (2) to give rise to further differentiated cells. This has been referred to as the kinetic definition.

Also, an operational definition of stem cell regards the stem cell as a colony-forming unit in various laboratory systems. For example, when suspensions of bone marrow (i.e., hematopoietic) cells are injected intravenously into heavily irradiated mice in which the spleen and marrow are reduced to stroma and are hematologically empty, discrete macroscopic colonies of cells are observed in the animal's spleen after 8-10 days.

A cell that meets any one of these three definitions of stem cell is considered to be a stem cell according to the present invention.

"Therapeutically effective amount": The term "therapeutically effective amount" refers to the amount of an agent needed to elicit the desired biological response. In the present invention, the agent is cells (e.g., stem cells, progenitor cells, etc.). The therapeutically effective amount of stem cells in a bone marrow transplant, for example, is enough cells to repopulate the bone marrow space and rescue the patient from aplastic anemia. In the case of gene therapy, the therapeutically effective amount of cells is the amount necessary to correct the recipient's underlying genetic defect. In the case of tissue damage or degeneration, the therapeutically effective amount of cells is the amount necessary to improve the function or structure of the abnormal tissue.

DETAILED DESCRIPTION OF CERTAIN PREFERRED EMBODIMENTS

The present invention provides a system for expanding a population of progenitor or stem cells under the condition of decreased p21 and/or p27 activity. These cells may then be used in pharmaceutical compositions in tissue transplants, bone marrow transplants, and/or gene therapy (e.g., stem cell gene therapy).

$p21^{cip1/waf1}$ $p21^{cip1/waf1}$ is a cyclin-dependent-kinase inhibitor (CKI). CKIs participate in the sequential activation and inactivation of cyclin-dependent kinases central to progression through the cell cycle (Sherr *Cell* 79:551-555, 1994; Sherr et al *Genes Dev* 9:1149-63, 1995; each of which is incorporated herein by reference). Specifically, the p21 gene has been found to play a key role in regulating the movement of cells from the $G_0$ to the $G_1$ stage of the cell cycle and therefore regulates the entry of stem cells into the cell cycle. By perturbing these regulatory circuits in stem cells the proliferation of stem cells is changed.

Targeted disruption of the p21 gene in mice resulted in cells which are impaired in their ability to achieve cell cycle arrest following irradiation (Brugarolas et al. *Nature* 377:552-7, 1995; Deng et al *Cell* 82:675-84, 1995; each of which is incorporated herein by reference), and antisense p21 has been shown to release human mesenchymal cells from $G_0$ (Nakanishi et al. *Proc. Natl. Acad. Sci. USA* 92:4352-6, 1995; incorporated herein by reference). Therefore, p21 plays a role in at least some cell types in the transition out of the cell cycle and maintenance in $G_0$. However, in hematopoiesis, levels of p21 have not been shown to be increased in CD34+ cells (Taniguchi et al. *Blood* 93:4167-4178, 1999; Yaroslavskiy et al *Blood* 93:2907-2917; 1999; each of which is incorporated herein by reference), and p21 –/– mice have not been noted to have an altered hematologic profile (Brugarolas et al. *Nature* 377: 552-557, 1995; Deng et al. *Cell* 82:675-84, 1995; each of which is incorporated herein by reference). Further, bone marrow progenitor cells from p21 –/– mice paradoxically have decreased proliferative ratios in response to cytokines (Mantel et al. *Blood* 88:3710-9b, 1996; Braun et al. *Blood Cells Mol. Dis.* 24:138-148, 1998; each of which is incorporated herein by reference). However, we found high levels of p21 mRNA when we assessed the quiescent stem cell-like fractions of bone marrow mononuclear cells. We therefore propose, although we do not wish to be bound by any particular theory, that p21 plays distinct roles in the subcompartments of the hematopoietic cascade—p21 seems to augment progenitor cell proliferation and to inhibit stem cell proliferation. By inhibiting the activity of p21, populations of hematopoietic stem cells are able to grow without inhibition (Cheng et al. "Hematopoietic Stem Cell Quiescence Maintained by $p21^{cip1/waf1}$" *Science* 287:1804-1808, Mar. 10, 2000; incorporated herein by reference).

p21 as used in the present invention can refer to either the gene and/or protein form of p21 or any homolog of p21, as will be clear from context. The homolog should be at least 50% homologous to the mouse p21 DNA or protein sequence, preferably 60% homologous, and more preferably 70% homologous. A homolog of p21 may also be identified by its activity such as being a cyclin dependent kinase inhibitor. In another preferred embodiment, the homolog of p21 is identified by its location in the genome (e.g., location on the chromosome).

$p27^{kip1}$

The protein p27 is a member of the cyclin dependent kinase inhibitor family, which includes p21, p27, and p57. p27 is molecularly distinct from p21 in its carboxy terminus, interacts with similar but not identical cyclin dependent kinases, and lacks p53 regulated expression (Polyak et al. "p27kip1, a cyclin-Cdk inhibitor, links transforming growth factor-beta and contact inhibition to cell cycle arrest" *Genes Dev* 8:9-22, 1994; Sherr et al. "Inhibitors of mammalian G1 cyclin-dependent kinases" *Genes Dev* 9:1149-63, 1995; Sherr "Cancer cell cycles" *Science* 274:1672-7, 1996; each of which is incorporated herein by reference). p27 acts by binding to and inhibiting the activation of cyclin E-Cdk2 and cyclin A-Cdk2 complexes. Characterization of the p27 protein and cloning and sequencing of the gene encoding the p27 protein are described in detail in PCT application (WO PCT/US95/07361), incorporated herein by reference.

Disruption of the p27 gene in mice led to a phenotype markedly different than the one of p21 –/– mice in that its body habitus is larger with hyperplasia of most organs (including hematopoietic organs), it spontaneously generates benign pituitary tumors, and it is infertile (Kiyokawa et al. "Enhanced growth of mice lacking the cyclin-dependent kinase inhibitor function of p27(Kip1)" *Cell* 85:721-732, 1996; Fero et al "A syndrome of multiorgan hyperplasia with features of gigantism, tumorigenesis, and female sterility in p27 (Kip 1)-deficient mice" *Cell* 85:733-744, 1996; Nakayama et al. "Mice lacking p27(Kip1) display increased body size, multiple organ hyperplasia, retinal dysplasia, and pituitary tumors" *Cell* 85:707-720, 1996; each of which is incorporated herein by reference). Like p21, however, p27 is associated with post-mitotic differentiation in some cell types (Asiedu et al. "Complex regulation of CDK2 during phorbol ester-induced hematopoietic differentiation" *Blood* 90:3430-3437, 1997; Liu et al. "Transcriptional activation of the human p21 (WAF1/CIP1) gene by retinoic acid receptor. Correlation with retinoid induction of U937 cell differentiation" *J. Biol Chem.* 271:31723-31728, 1996; Kranenburg et al. "Inhibition o cyclin-dependent kinase activity triggers neuronal differentiation of mouse neuroblastoma cells" *J Cell Biol.* 131:227-234, 1995; each of which is incorporated herein by reference) and antisense p27 can suppress cell cycle arrest in mesenchymal cells (Coats et al. "Requirement of p27Kip1 for restriction point control of the fibroblast cell cycle" *Science* 272:877-880, 1996; Rivard et al. "Abrogation of p27Kip1 by cDNA antisense suppresses quiescence (GO state) in fibroblasts" *J Biol. Chem.* 271:18337-18341, 1996; each of which is incorporated herein by reference).

Unlike p21, p27 is controlled by both translational and posttranslational mechanisms (Hengst et al. "Translation control of p27Kip1 accumulation during the cell cycle" *Science* 271:1861-1864, 1996; Pagano et al. "Role of the ubiquitin-proteasome pathway in regulating abundance of the cyclin-dependent kinase inhibitor p27 [see comments]" *Science* 269:682-685, 1995; each of which is incorporated herein by reference). A role for p27 in hematopoiesis is supported by direct flow cytometric evidence for expression in primitive cells (Tong et al. "TGF-βsuppresses cell division of Go CD34+cells while maintaining primitive hematopoietic potential" *Exp. Hematol.* 26:684, 1998; incorporated herein by reference), expression in more mature progenitors (Taniguchi et al. "Expression of p21 (Cip1/Waf1/Sdi1) and p27 (Kip1) cyclin-dependent kinase inhibitors during human hematopoiesis" *Blood* 93:4167-4178, 1999; Yaroslavskiy et al. "Subcellular and cell-cycle expression profiles of CDK-inhibitors in normal differentiating myeloid cells" *Blood* 93:2907-2917, 1999; each of which is incorporated herein by reference) and indirectly by improved retroviral transduction in the context of anti-sense p27 (Dao et al. "Reduction in levels of the cyclin-dependent kinase inhibitor p27(kip 1) coupled with transforming growth factor beta neutralization induces cell-cycle entry and increases retroviral transduction of primitive human hematopoietic cells [In Process Citation]" *Proc. Natl. Acad. Sci. USA* 95:13006-13011, 1998; incorporated herein by reference). As shown in the Examples below, disruption of the p27 gene allows for expansion of a population of progenitor cells in vivo as well as ex vivo. In terms of gene therapy, a minority population of stem cells with less than wild type p27 activity tends to predominate the progenitor and mature blood cell compartments without leading to leukemia and polycythemia.

p27 as used in the present invention can refer to either the gene or protein form of p27 or any homolog of p27, as will be clear from context. The homolog should be at least 50% homologous to the mouse or human p27 DNA or protein sequence. A homolog of p27 may also be identified by its activity such as being a cyclin dependent kinase inhibitor. In another preferred embodiment, the homolog of p27 is identified by its location in the genome (e.g., location on the chromosome).

Stem Cells/Progenitor Cells

The stem cells or progenitor cells used in the present invention may be obtained from any tissue of an animal or plant at any stage of development. The cells may be derived from lung, gastrointestinal tract, liver, kidney, neural, skin, muscle, cardiac muscle, bone, mesenchymal, or hematopoietic tissue. In certain embodiments of the present invention, the cells are obtained from embryonic or fetal tissues. The cells may not be committed to a single tissue or may be able to produce differentiated cells in a variety of tissues such as lung and gastrointestinal tract, or skin and neural tissue. Cells obtained from embryonic or fetal tissues would be expected to have a greater potential than most cells found in adult animals.

The cells may be obtained from any animal or plant. Preferably, the animal is a mammal, and humans are particularly preferred. When the cells are to be eventually used in treating a patient, the stem cells are preferably obtained from the same species as the animal to be treated. More preferably, the cells are obtained from the patient or a close relative. In the most preferred embodiment, the cells are autologous. In another preferred embodiment, the stem cells are obtained from a cell culture or tissue culture. These cells may be from a donor or from established cell lines. The stem cells utilized in the present invention can be purified using any available method such as, for example, fluorescence-activated cell sorter (FACS) analysis, immunomagnetic bead purification (or other immunoprecipitation method), or functional selection using anti-metabolites, dye exclusion, resistance to cytokines, or attachment to lectins or other binding molecules.

In a particularly preferred embodiment of the present invention, the cells are hematopoietic cells. The hematopoietic cells may be obtained from any source. Preferably the cells are obtained from the hematopoietic tissue of an animal. Preferably the animal is a mammal. More preferably the mammal is a rat, mouse, rabbit, guinea pig, ferret, dog, cat, etc. In other preferred embodiments, the mammal is a human. The bone marrow is typically the site where hematopoietic stem cells or progenitor cells are found; however, the spleen, liver, thymus, lymph nodes, umbilical cord blood, and blood may also be used to obtain the cells. The cells utilized in the present invention can be purified using any available method such as, for example, fluorescence-activated cell sorter (FACS) analysis, immunomagnetic bead purification (or other immunoprecipitation method), or functional selection using anti-metabolites.

When the stem cells are to be used in a bone marrow transplant or in stem cell gene therapy, the stem cells are preferably obtained from the same species as the animal to be treated. More preferably, the cells may be obtained by a biopsy such as a bone marrow biopsy from the patient or a close relative. In the most preferred embodiment, the cells are autologous. In another embodiment, the stem cells may be obtained from a cell culture or tissue culture. These cells may be from a donor or from established cell lines.

The cells used in the present invention may be pluripotent hematopoietic stem cells or may be cells committed to one particular lineage. For example, the cell may be committed to erythropoiesis, granulopoiesis, or thrombopoiesis. A pluripotent cell may give rise to all types of blood cells including erythrocytes, platelets (thromobocytes), polymorphonucleated neutrophils, monocytes, macrophages, eosinophils, basophils, mast cells, B-cells, plasma cells, and T-cells. A myeloid stem or progenitor cell is more committed than the pluripotent cells and is only able to give rise to erythrocytes, platelets (thrombocytes), polymorphonucleated neutrophils, monocytes, macrophages, eosinophils, basophils, and mast cells. A lymphoid stem or progenitor cell only gives rise to T-cells, B-cells, and plasma cells.

Inhibition of p21 and/or p27

Any method may be used in the current invention to decrease the activity or amount of p21 and/or p27. These methods include, but are not limited to, altering the transcription, translation, and/or enzymatic activity of p21 or p27. Examples of altering the transcription include disrupting the gene, altering the regulatory sequence of the p21 or p27 gene (e.g., promoter, enhancer), adding antisense p21 or p27 agents to the cells, etc. The splicing of the primary transcript may also be changed by altering the splicing signals of the transcript. The translation may be affected by altering the Shine-Delgarno sequence of the transcript, altering the codon usage in the mRNA transcript, adding antisense p21 or p27 agents to the cells, etc. The enzymatic activity of the p21 or p27 protein may be altered, for example, by contacting the protein with a known inhibitor, contacting the protein with an antibody known to inhibit p21 or p27 activity, adding an allosteric effector, inhibiting post translational modifications of the protein, etc. Also, the complexes to which p21 or p27 binds or the kinase that it inhibits and that can overwhelm its inhibitory function can be altered to create the same net effect as is seen with decreased p21 or p27 activity.

When p21 or p27 activity is inhibited in the cell, the stem or progenitor cell can enter the cell cycle and proliferate expanding the population of cells. Preferably, the inhibition may be stopped or decreased after the population of cells has been expanded to the desired number.

In a preferred embodiment, the p21 or p27 activity of the cell is inhibited by an agent known to inhibit the kinase inhibiting activity of p21 or p27. These agents may be peptides, aptamers, proteins, non-peptide chemical compounds, polynucleotides, carbohydrates, etc. These inhibitors of p21 or p27 activity are preferably specific for p21 or p27 and do not interact with and/or inhibit other proteins (e.g., cyclin-dependent-kinase inhibitors) in the cells. In a particularly preferred embodiment, these agents are hydrophobic enough to diffuse through the plasma membrane of the cells or are taken up by the cells. Alternatively, the agents may be delivered into the cell via microinjection or lipofection.

In another preferred embodiment, the inhibitory agent is an antibody, or fragment thereof. Preferably, the antibody is specific for p21 or p27. The antibody's may bind to any location on p21 or p27 as long as the binding of the antibody results in a decrease in p21 or p27 activity. A preferred binding site on p21 or p27 includes the active site (i.e., where the p21 or p27 protein binds to the kinase). The antibody may be a whole antibody, a fragment, an antibody conjugated to another agent, etc. Preferably, the antibody is monoclonal. In another preferred embodiment, the antibody has been engineered to get into the stem cell or progenitor cell.

Antisense therapy is meant to include, e.g., administration or in situ provision of single-or double-stranded oligonucleotides or their derivatives which specifically hybridize, e.g., bind, under cellular conditions, with cellular mRNA and/or genomic DNA encoding p21 or p27, or mutants thereof, so as to inhibit expression of the encoded protein, e.g., by inhibiting transcription and/or translation (Crooke "Molecular mechanisms of action of antisense drugs" *Biochim. Biophys. Acta* 1489(1):31-44, 1999; Crooke "Evaluating the mechanism of action of antiproliferative antisense drugs" *Antisense Nucleic Acid Drug Dev.* 10(2):123-126, discussion 127, 2000; *Methods in Enzymology* volumes 313-314, 1999; each of which is incorporated herein by reference). The binding may be by conventional base pair complementarity, or, for example, in the case of binding to DNA duplexes, through specific interactions in the major groove of the double helix (i.e., triple helix formation) (Chan et al. *J Mol. Med.* 75(4): 267-282, 1997; incorporated herein by reference).

In certain preferred embodiments, the antisense construct binds to a naturally-occurring sequence of a p21 or p27 gene which, e.g., is involved in expression of the gene. These sequences include, e.g., start codons, stop codons, and RNA primer binding sites.

An antisense construct of the present invention can be delivered, e.g., as an expression plasmid or viral vector which, when transcribed in the cell, produces RNA which is complementary to at least a unique portion of the cellular mRNA which encodes a p21 or p27 protein. An alternative is that the antisense construct is an oligonucleotide probe which is generated ex vivo and which, when introduced into the cell causes inhibition of expression by hybridizing with mRNA and/or genomic sequences of a p21 or p27 gene. The antisense construct may be introduced into the cell via microinjection, lipofection, passive diffusion, or facilitated transport by chaperone molecules or molecules such as HIV tat, or peptides thereof (Schwarze et al. *Science* 285:1569-1572, 1999; incorporated herein by reference). Such oligonucleotide probes are preferably modified oligonucleotides which are resistant to endogenous nucleases, e.g., exonucleases and/or endonucleases, and are therefore stable in vivo. Exemplary nucleic acid molecules for use as antisense oligonucleotides are phosphoramidate, phosphothioate, o-methylated, and methylphosphonate analogs of DNA (U.S. Pat. Nos. 5,176,996; 5,264,564; and 5,256,775; each of which is incorporated herein by reference). Additionally, general approaches to constructing oligomers useful in antisense therapy have been reviewed (van der Krol et al. *Biotechniques* 6:958-976, 1998; Stein et al. *Cancer Res.* 48:2659-2668, 1988; each of which is incorporated herein by reference).

Pharmaceutical Composition

The cells of the present invention may be used in a pharmaceutical composition. The cells may have a normal to decreased p21 and/or p27 activity. The cells may be used in immunotherapy, bone marrow transplants, tissue transplants, or gene therapy (e.g., stem cell gene therapy). An exemplary pharmaceutical composition comprises a therapeutically effective amount of cells, optionally combined with a pharmaceutically-acceptable excipient. The stem cells, progenitor cells, or other cells may or may not have been transfected, transformed, or infected. In certain preferred embodiments, the cells have altered by the hands of man.

The pharmaceutical compositions of the present invention may be administered by any known method including, for example, intravenous, intramuscular, subcutaneous, intrasternal, intraosseous, and parenteral administration. A more preferable mode of administration is parenteral administration, and the most preferred method of parenteral administration is intravenous administration. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono or diglycerides. In addition, fatty acids such as oleic acid are commonly used in the preparation of injectables.

Transgenic Animal or Plant

The present invention provides for transgenic animals and plants with alterations of the p21 and/or p27 gene(s). In a particularly preferred embodiment of the present invention, the transgenic animal or plant has at least one copy of the p21 gene altered in at least one of the cells of the organism. In other embodiments, both copies of the p21 gene have been altered. The present invention provides for a transgenic animal or plant with at least one copy of the p21 gene and the p27 gene altered (i.e., mutated, changed, or disrupted) in at least one of the cells of the organism. In other embodiments both copies of the p21 gene and/or the p27 gene have been altered. The transgenic organism of the present invention may also have other genomic alterations in addition to the p21 and/or p27 mutations. The term transgenic animal or plant is meant to include an organism that has gained new genetic material from the introduction of foreign DNA, i.e., partly or entirely heterologous DNA, into the DNA of its cells; or introduction of a lesion, e.g., an in vitro induced mutation, e.g., a deletion or other chromosomal rearrangement into the DNA of its cells; or introduction of homologous DNA into the DNA of its cells in such a way as to alter the genome of the cell into which the DNA is inserted, e.g., it is inserted at a location which differs from that of the natural gene or its insertion results in a knockout. The organism may include a transgene in all of its cells including germ line cells, or in only one or some of its cells.

In certain embodiments, the transgenic animal or plant has a p21 and/or p27 transgene, or fragment or analog thereof. In certain other embodiments, the transgenic animal has a knockout for the p21 and/or p27 gene. In a preferred embodiment of the present invention, at least one of the hematopoietic stem or progenitor cells of the transgenic animal has at least one copy of the p21 and/or p27 gene that has been changed, mutated, or disrupted.

Gene Therapy

The stem cells, progenitor cells, or other cells of the present invention with less than wild type p27 activity and, optionally less than wild type p21 activity, may be particularly useful in gene therapy, bone marrow transplants, and tissue repair/regeneration. In certain preferred embodiments, the cells to be administered in a pharmaceutical compositions suitable for gene therapy have had their genomes altered by the hands of man in order to correct a genetic defect or to insert a transgene. Given the ability of a minority population of p27 −/− stem cells to predominate in the progenitor and mature blood cells compartments as described below in the Example 2, the number of cells needed to improve the signs and symptoms of the genetic defect is preferably far less than is normally required in stem cell gene therapy. This ability of p27 −/− cells to expand in vivo and compete out wild type cells or cells without the desired alteration allows one to treat diseases that require a high efficiency of gene transfer and/or gene effect (e.g., sickle cell anemia). In a particularly preferred embodiment, the number of cells with the corrected genetic defect or with the transgene inserted is less than 50% of the total number of cells transplanted. More preferably, the number of cells is less than 75% of the total number of transplanted cells, and most preferably, the number of cells is less than 90% of the total number of cells transplanted.

In another particularly preferred embodiment, the number of transplanted cells with altered genomes is sufficient to allow the cell population to expand in vivo and compete out other wild type cells. This allows one to transplant a small number of cells initially, but have the cells derived from the transplanted cells dominate the cell population in the transplanted individual after a set amount of time (e.g., weeks, months, years depending on the cell type being transplanted). In certain preferred embodiments, the percentage of cells derived from the transplanted cells and/or having the desired alteration in their genome may reach at least 50%, 75%, 80%, 90%, 95%, or 99% of that particular cell population in the transplanted individual.

In a particularly preferred embodiment, both the activities of p27 and p21 are less than the activities found in wild type cells. The decreased p21 activity allows for proliferation in the stem cell compartment while the decreased p27 activity allows for proliferation in the progenitor cell compartment. In another preferred embodiment, the inhibition of the activity for one or both of the cyclin-dependent kinase inhibitors is temporary.

In another particularly preferred embodiment, cells from tissues other than hematopoietic tissue may be used in the regeneration of other organs or tissues. For example, neural cells may be used to regenerate neural tissues, or pluripotent stem cells may be used to regenerate a number of different tissues.

These and other aspects of the present invention will be further appreciated upon consideration of the following Examples, which are intended to illustrate certain particular embodiments of the invention but are not intended to limit its scope, as defined by the claims.

EXAMPLES

Example 1

Hematopoietic stem cell quiescence in vivo is maintained by p21$^{cip1/waf1}$ and is critical for preventing premature exhaustion of hematopoiesis Methods Generation of homozygous mice. Heterozygote 129/SV p21 +/− mice (Brugarolas et al. *Nature* 377:552-7, 1995; incorporated herein by reference) were obtained from the laboratory of Tyler Jacks (MIT, Boston) under the permission of the Subcommittee on Research Animal Care of the Massachusetts General Hospital (MGH). The mice were housed in sterilized microisolator cages and received autoclaved food and drinking water at the MGH animal care facility. The inbred 129/SV heterozygotes (+/−) were bred to yield homozygous and wild-type offspring. The litter mates from the same +/− parents were used in each experiment.

Mouse genotyping. Genotyping was achieved by DNA PCR. Briefly, genomic DNA was isolated from tail biopsy and analyzed by amplification using three primers: p21 +116F (AAG CCT TGA TTC TGA TGT GGG C). (SEQ. ID NO. 1), p21−135 (TGA CGA AGT CAA AGT TCC ACC G). (SEQ ID NO. 2), and Neo 19+ (GCT ATC AGG ACA TAG CGT TGG C), (SEQ ID NO. 3). p21 +116F was involved in the amplification of both mutant and wild-type alleles. The conditions for thermocycling were as follows:

Step 1: 94° C. for 4 min.
Step 2: 94° C. for 1 min.
Step 3: 64° C. for 1 min.
Step 4: 72° C. for 2 min.
Step 5: Repeat step 2-4 forty times
Step 6: 72° C. for 2 min.

Diagnostic mutant and wild-type band were 750 bp and 900 bp, respectively, by 2.0% agarose gel electrophoresis.

Bone marrow sampling. Mouse bone marrow was obtained from 8-12-week-old animals from each group (−/−, +/+) sacrificed with $CO_2$. The marrow cell suspensions were flushed from femurs and tibias, filtered with 100-mesh nylon cloth (Sefar America, Inc., Kansas City, Mo.), and stored on ice until use.

Flow cytometric analysis. Flow cytometry was used to quantify the cell cycle status in the stem cell compartment. Bone marrow nucleated cells were labeled with biotinylated anti-lineage antibodies (CD3, CD4, CD8, B220, Gr-1, Mac-1 (Caltac), TER-119 (Pharmingen)) and streptavidin-FITC, then incubated with 1.67 μmol/L DNA dye, Hoechst 33342 (Hst), and 1 μg/ml RNA dye, Pyronin Y (PY), at 37° C. for 45 minutes, respectively. Flow cytometry was performed on FACSVantage Instruments (Becton Dickinson).

Colony forming assay. Bone marrow nuclear cells were cultured in 0.8% methylcellulose, 30% fetal bovine serum, 1% bovine serum albumin 0.1 mM 2-mercaptoethanol, 2.0 mM L-glutamine of α-MEM semi-solid matrix culture medium (StemCell Technologies, Inc.) with cytokine combinations of 50 ng/ml hu-SCF (R & D System Inc.), 20 ng/ml mu-IL-3 (Genzyme), 20 ng/ml hu-IL-6 (Genzyme), 50 ng/ml hu-G-CSF (R & D System Inc.), 20 ng/ml hu-GM-CSF (R & D System Inc.), and 2 U/ml hu-Epo (Amgen). Cells were placed at 20,000/200 μl/well into 48-well plates and placed at 37° C., 5% $CO_2$. At day 10, myeloid and erythroid colonies were scored, totaled, and reported as CFCs.

Long-term culture with limiting dilution. To quantify the stem cells, we adapted the cobblestone area forming cell (CAFC) assay (Ploemacher et al. *Blood* 74:2755-2763, 1989; incorporated herein by reference) with minor modifications as follows. To prepared stromal layers, murine bone marrow nucleated cells were cultured at 33° C. in long term culture (LTC) medium (α-MEM with 12.5% mouse serum, 12.5% fetal bovine serum, 0.2 mM I-inositol, 20 mM folic acid, $10^{-4}$ M 2-mercaptoethanol, 2 mM L-glutamine, and $10^{-6}$ M hydrocortisone). After 2 weeks, confluent stromal layers were trypsinized, irradiated (15 Gy), and subcultured in 96-well flat-bottomed plates at a density of $2.5 \times 10^4$/well. Cultures were then seeded with serially diluted single-cell suspensions of femoral marrow in the same medium. Marrow pooled from two to ten animals of each type was seeded at 2-fold dilutions ($10^5$ - 1562 cells/well) for nucleated bone marrow cells. Cultures were very gently re-fed with 50 µl medium after semi-depletion weekly and the CAFCs and/or blast colonies (Ploemacher et al. *Blood* 74:2755-2763, 1989; Muller-Sieburg et al. *J Exp. Med.* 183:1141-50, 1996; incorporated herein by reference) were scored until the 6th week.

5-FU exposure in vivo. The anti-metabolite, 5-FU, was used to selectively deplete cycling cells in vivo. 5-FU was administered i.p. weekly at a dose of 150 mg/kg and the survival rates of the groups defined. To more specifically test the effect of p21 on hematopoietic cells, we transplanted bone marrow cells from p21 −/− or p21 +/+ animals into lethally irradiated mice of the same genetic background (p21 +/+, 129/SV, 8 weeks old, Jackson), allowing the hematopoietic and immune system to repopulate for one month, and then observed the 5-FU effects on those animals. To test the sensitivities of primitive hematopoietic cells, a single injection of 5-FU i.v. at a dose of 200 mg/kg was administered and cells for long-term culture with limiting dilution were obtained one day after the injection.

Serial bone marrow transplantation. Serial bone marrow transplantation (Harrison et al. *J Exp. Med.* 147:1526-1531, 1978; Harrison *Blood* 55:77-81, 1980; Harrison et al. *J Exp. Med.* 156:1767-1779, 1982; Harrison et al. *J Exp. Med.* 172: 431-437, 1990; each of which is incorporated herein by reference) was used to evaluate the ability of stem cells to self-renew. Male mice (8-12 weeks old) were used as marrow donors and the marrow cells prepared as above. Female recipient mice (8-10 weeks old, 129/SV, Jackson laboratory) were lethally irradiated using a Mark 1-Model $25^{137}$ Cesium Irradiator (JL Shepherd and Associates, San Fernando, Calif.) with 10 Gy whole body irradiation (WBI) at 5.96 Gy/min. One to two million nucleated cells in 1 ml 199 Medium were injected intravenously through 27 gauge needles into the lateral tail veins of warmed recipients. Recipient mice were monitored daily for survival for more than 30 days in which stem cells have been noted by others to account for hematopoietic recovery following lethal irradiation (33). The mice were sacrificed at 2-4 months and bone marrow cells were prepared from those sacrificed mice and injected into new female recipients. This process was repeated for 4 sequential transplants with survival frequency plotted for each group. Long-term culture with limiting dilution described above was performed on the donor cells of each transplant to quantify the frequencies of hematopoietic progenitors and stem cells.

Semi-quantitative DNA PCR for Y-chromosome. The contribution of the original donor cells was monitored by a PCR-based semi-quantitative analysis for Y-chromosome specific sequence (Sry) (Muller et al. *Development* 118:1343-51, 1993; incorporated herein by reference) using an aliquot of each marrow sample described below. Briefly, DNA from bone marrow cells was isolated using a Puregene kit (Gentra System, Inc., Research Triangle Park, NC) according to the manufacturer's instruction. 200 ng of DNA was applied to the PCR reaction. The sequences for the PCR primers are as follows (5'-3'): Sry primers: (TCA TGA GAC TGC CAA CCA CAG), (SEQ ID NO. 4), and (CAT GAC CAC CAC CAC CAC CAA). (SEQ ID NO. 5); myogenin primers: (TTA CGT CCA TCG TGG ACA GC), (SEQ ID NO. 6), and (TGG GCT GGG TGT TAG TCT TA), (SEQ ID NO. 7). The PCR cycles were: 10 min 94° C., 35 cycles of 94° C. for 10 sec, 65° C. for 30 sec followed by 5 mm 72° C. A linear relationship between the ratios of male genomic DNA to the total amount of DNA and the signal intensities of the PCR product was plotted simultaneously in order to quantify the contribution of donor cells.

Homing assay. Donor marrow nucleated cells were stained with the cytoplasmic dye, CFDA SE (CFSE) according to the manufacturer's instruction (Molecular Probes, Eugene, Oregon) and $2 \times 10^7$ CFSE stained cells were injected into lethally irradiated recipient mice. Spleen and bone marrow were harvested 9 hours after injection and cells stained with lineage markers and anti-Sca-1 antibody prior to flow cytometric analysis Statistical analysis. Results from survival experiments were analyzed using a log-rank nonparametric test and expressed as Kaplan-Meier Survival curves (Grzegorzewski et al. *J Exp Med* 180:1047-57, 1994). The significance of the difference between groups in the in vitro culture were evaluated by analysis of variance followed by a two-tailed Student's test.

Results

The direct impact of p21 on the stem cell compartment was assessed using mice engineered to be deficient in p21. The cell cycling status of stem cells was determined using the RNA dye, pyronin Y (PY), as a measure of quiescence among the lineage negative (lin⁻) (Spangrude et al. *Science* 241:58-62, 1988; incorporated herein by reference) and Hoescht 33342 $(Ho)^{low}$ staining bone marrow cells (Leemhuis et al. *Exp. Hematol.* 24:1215-1224, 1996; incorporated herein by reference). Cells from p21 −/− animals consistently demonstrated a smaller fraction in the PY low portion of the continuum (FIG. 1) (p=0.005, n=6) suggesting that p21 does function to impede the entry of stem cells into active cell cycle. Independently, rhodamine (Rho), a mitochondrial dye, and Ho were used to define the population of cells with low levels of metabolic activity and exclusion of Ho corresponding to a quiescent stem cell pool (Wolf et al. *Exp. Hematol.* 21:614-22, 1993; incorporated herein by reference). The $Rho^{low}/Ho^{low}$ population of $lin^-Sca-1^+$ cells was also smaller in the p21 −/− animals (p=0.07, n=3) confirming this observation.

Figure 2A:
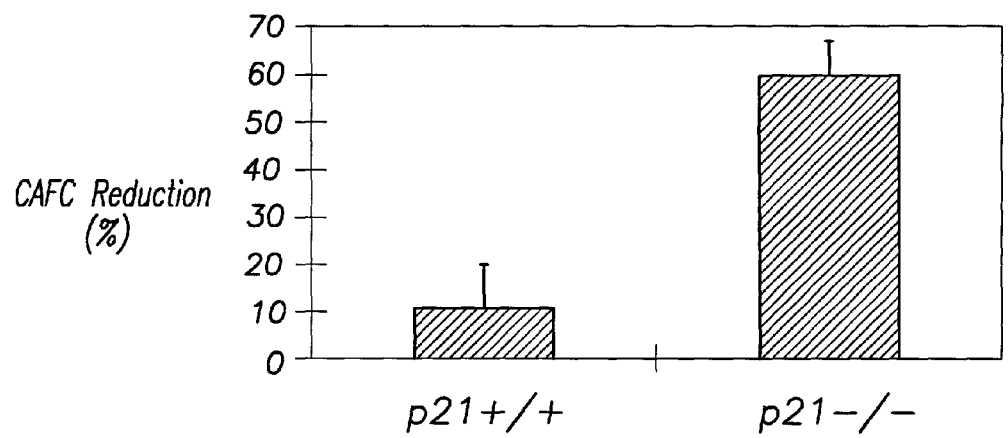
FIG. 2. Response of p21 −/− mice to 5-FU treatment in vivo demonstrates a higher cycling status and increased sensitivity to toxic injury. a. CAFC reduction after a 5-FU pulse. A single intravenous injection of 5-FU at the dose of 200 mg/kg was performed, and cells for long-term culture with limiting dilution were obtained one day after the injection. CAFCs were counted at week 5. Y axis values=[(CAFCs from un-treated mice−CAFCs from 5-FU treated mice)/CAFCs from un-treated mice]×100%. Data represent the mean from three independent experiments. Three litter mates for each genotype were used in each experiment and 3-5 limiting dilutions were applied for each sample. The student's test was used to analyze the data (n=3, p=0.0019). b. Survival outcome after sequential 5-FU treatment. 5-FU was administered i.p. weekly at dose of 150 mg/kg, and the survival rates of the groups were defined. Results were analyzed using a log-rank nonparametric test and expressed as Kaplan-Meier Survival curves (n=10, p=0.0054).

To further define this issue, we pulsed −/− or +/+ mice with 200 mg/kg of the anti-metabolite, 5-fluorouracil (5-FU), to selectively kill cycling cells (Berardi et al. *Science* 267:104-108, 1995; Lemer et al. *Exp. Hematol.* 18:114-118, 1990; each of which is incorporated herein by reference). Marrow was harvested one day after 5-FU injection and long term co-culture or cobblestone area-forming cell (CAFC) assays performed. These assays linearly correlate with in vivo repopulating potential (Ploemacher et al. *Blood* 78:2527-2533, 1991; Ploemacher et al. *Blood* 74:2755-2763, 1989; each of which is incorporated herein by reference) and were used here as a stem cell assay instead of competitive repopulation assays given the lack of a congenic mouse strain with 129/SV background. A significant reduction of CAFCs was noted after a pulse of 5-FU in the −/− group compared with the +/+ group controls (60.5% vs. 10.8%, p=0.0019) (FIG. 2a).

Figure 2B:
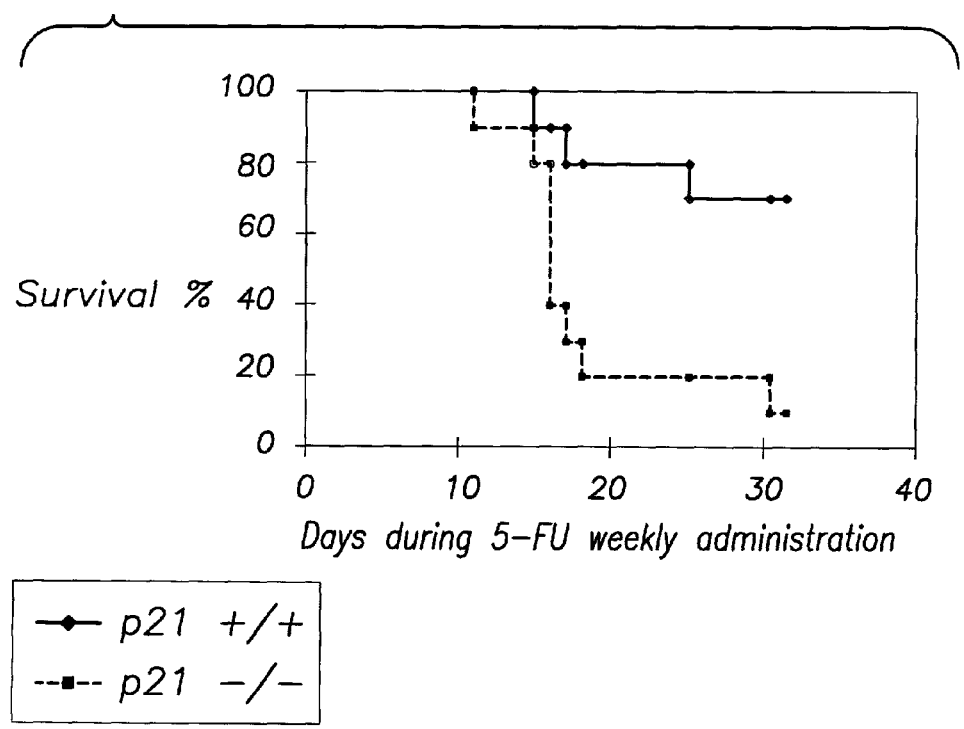

When the animals were given 5-FU weekly as a challenge to assess the relative restriction on cell cycle entry of primitive cells, the survival percentage in the −/− group was much lower than in litter mate +/+ controls (10% vs 70% in one month, p=0.0054) (FIG. 2b). To exclude the possible influence of toxicity to other tissues, we repopulated the hematopoietic system of lethally irradiated +/+ hosts with either +/+ or −/− bone marrow cells. One month after transplantation, we challenged the reconstituted animals with an identical protocol of sequential 5-FU treatment. A similar relative survival pattern was observed with mice carrying the −/− hematopoietic system demonstrating markedly increased mortality compared with those with a +/+ hematopoietic system (p=0.0089). Therefore, death was due to hematopoietic and not other tissue sensitivity to antimetabolite treatment. Thus p21 restricts the entry of stem cells into cycle and protects hematopoietic cells from destruction by cell cycle dependent myelotoxic agents.

We next sought to determine whether the lack of p21 resulted in an increase in stem cell number in the basal state or a decline due to more rapid depletion. The relative number of stem cells present in wild type versus p21 −/− mice was directly measured by limit dilution CAFC assays. A significant increase in primitive cells in the p21 −/− animals (Table 1, p=0.0393, n=7) was noted. Thus, p21 provides a dominant negative effect which is sufficient to inhibit stem cell cycling. In the absence of p21, the inhibition is alleviated, leading to an expansion of the primitive cell pool under resting conditions. In contrast, no significant differences in colony forming cells, bone marrow cellularity and white blood cells were noted (Table 2, 3, and 4) implying that p21 has a differentiation stage specific function in hematopoietic stem cells. The paradoxical pro-proliferative effect of p21 in more mature progenitors observed by others, may balance the inhibitory influence p21 enforces on stem cells (Mantel et al. *Blood* 88:3710-9b, 1996; Braun et al. *Blood Cells Mol Dis.* 24:138-148, 1998; each of which is incorporated herein by reference). This apparent dichotomy may reflect the complex biochemical role p21 has been noted to play as either requisite participant in cyclin-CDK complex formation necessary for movement of the cell through late $G_1$ into S, or as CKI inhibiting entry into S phase (LaBaer et al. *Genes Dev.* 11:847-862, 1997; incorporated herein by reference). We speculate that p21 plays a central role in determining the known differential sensitivity of stem cells versus progenitor cells to proliferative stimuli and that the p21 effect represents a uniquely bimodal functional distinction between these two broad classes of cells.

TABLE 1

Comparison of CAFCs scored at week 5 between p21 +/+ and −/− mice (per $10^5$) demonstrates increased stem cell numbers. Each pair was pooled from 2-3 −/− or +/+ litter mate mice in each experiment. Each data point was generated from 3-5 limiting dilutions and data was analyzed using the paired t-test.

|  | P21 +/+ | p21 −/− |
| --- | --- | --- |
| Experiment 1 | 2.88 | 4.98 |
| Experiment 2 | 2.41 | 5.29 |
| Experiment 3 | 0.83 | 1.06 |
| Experiment 4 | 0.58 | 0.92 |
| Experiment 5 | 0.18 | 0.49 |
| Experiment 6 | 0.87 | 1.33 |
| Experiment 7 | 0.32 | 1.25 |
| Mean | 1.15 | 2.19 |
| p value, paired t-test | 0.0393 | |

TABLE 2

Comparison of CFCs between p21 +/+ and −/− mice (per $10^4$) indicates no difference in progenitors. Data represents colony forming ability at day 10. Each pair was pooled from 2-3 −/− or +/+ litter mate mice in each experiment. Each data point was generated from at least 4 replicates and data were analyzed using the paired t-test.

|  | P21 +/+ | p21 −/− |
| --- | --- | --- |
| Experiment 1 | 66.65 | 50.00 |
| Experiment 2 | 76.25 | 35.00 |
| Experiment 3 | 60.00 | 45.00 |
| Experiment 4 | 55.00 | 80.00 |
| Experiment 5 | 51.84 | 56.50 |
| Experiment 6 | 42.33 | 35.67 |
| Experiment 7 | 32.67 | 35.00 |
| Mean | 53.38 | 46.61 |
| p value, paired t-test | 0.1755 | |

TABLE 3

Comparison of total cell number per bone marrow harvest between p21 +/+ and −/− mice indicates no difference in cellularity. Each data point represents the mean from 1-3 −/− or +/+ litter mate mice in each experiment. total cell number ($\times 10^7$/femur pair) was counted from each harvest and data were analyzed using the paired t-test.

|  | P21 +/+ | p21 −/− |
| --- | --- | --- |
| Experiment 1 | 1.4 | 1.3 |
| Experiment 2 | 1.58 | 1.76 |
| Experiment 3 | 2.5 | 2.08 |
| Experiment 4 | 1.5 | 1.5 |
| Experiment 5 | 1.63 | 1.27 |
| Experiment 6 | 1.29 | 2.14 |
| Mean | 1.63 | 1.68 |
| p value, paired -t-test | 0.8284 | |

TABLE 4

Comparison of blood cell counts between p21 +/+ and −/− mice (n = 10, Mean ± SD) indicates no significant difference in mature cell populations. Blood was collected by tail bleeding. All the blood counts were performed and analyzed using the t-test for two samples with the same variance.

|  | WBC ($\times 10^3$/ul) | RBC ($\times 10^6$/ul) | PLT ($\times 10^3$/ul) |
| --- | --- | --- | --- |
| p21 +/+ | 5.38 ± 2.95 | 9.08 ± 0.86 | 444.60 ± 55.99 |
| p21 −/− | 7.48 ± 1.83 | 9.38 ± 0.96 | 510.10 ± 141.65 |
| p value | 0.0670 | 0.2290 | 0.0950 |

Figure 3A:
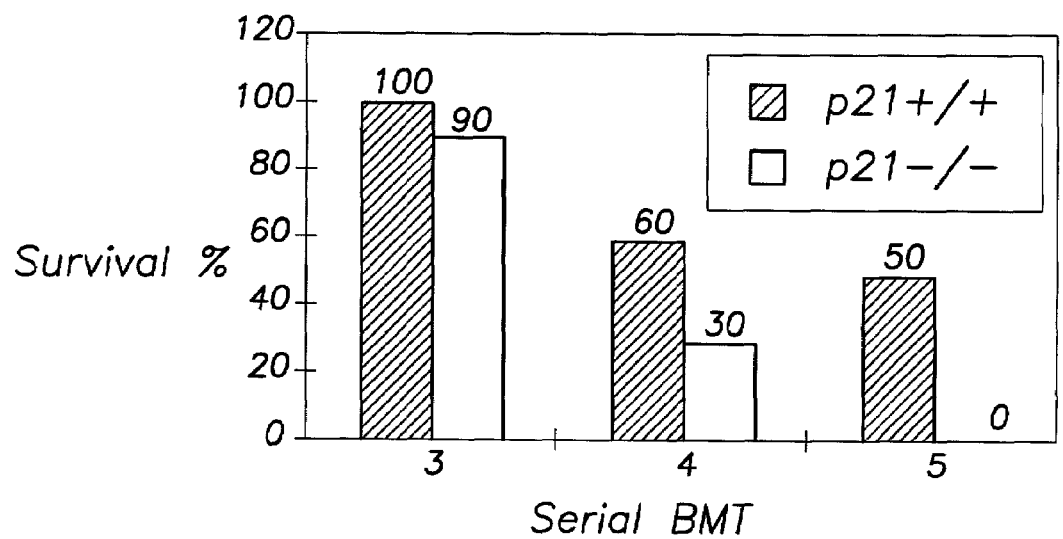
FIG. 3. Animal survival after serial bone marrow transplantation (BMT) demonstrates reduced self-renewal of hematopoietic potential. Male mice were used as marrow donors. Female recipient mice were lethally irradiated with 10 Gy whole body irradiation (WBI) at 5.96 Gy/min. Two million nucleated cells were injected intravenously into the lateral tail veins of warmed recipients. Recipient mice were monitored daily for survival for more than one month. The mice were sacrificed after 2-4 months, and bone marrow cells were prepared from those sacrificed and injected into new female irradiated recipients. This process was repeated for an additional four times. a. Cumulative survival after serial BMT. Each group included 10 mice initially. The donor marrow from the previous transplant was injected into a new recipient individually and therefore the actual recipient number was reduced during the serial transplantation. The ratio between actual survival animal number at each BMT and the total number at $1^{st}$BMT is plotted as survival % (Y axis value). b. Radiation-protection of the marrow from the $4^{th}$BMT. $5 \times 10^5$ cells from the $4^{th}$BMT mice were transplanted into the lethally irradiated recipients described as above and survival data were analyzed using a log-rank nonparametric test and expressed as Kaplan-Meier Survival curves (n=6/each group, p=0.002). Similar results were obtained at lower doses ($10^5$) of donor cells (n=10/each group, p=0.008, curve not shown). c. Donor contribution monitored by PCR. The contribution of the original donor cells was monitored by a PCR-based semi-quantitative analysis for Y-chromosome specific sequence (Sry) using an aliquot of marrow sample from each transplant. DNA was prepared from donor cells collected at the $4^{th}$ transplant and 200 mg was used for the PCR analysis. 2% agarose gel was used to display the PCR products. Left panel in the left gel shows the positive controls which have been mixed with male and female DNA at the ratios indicated. Complete contribution from donor cells was further confirmed by p21 genotyping PCR shown at the right gel. Similar results were obtained from the $1^{st}$, $2^{nd}$, and $3^{rd}$ transplant (data not shown).
Figure 3B:
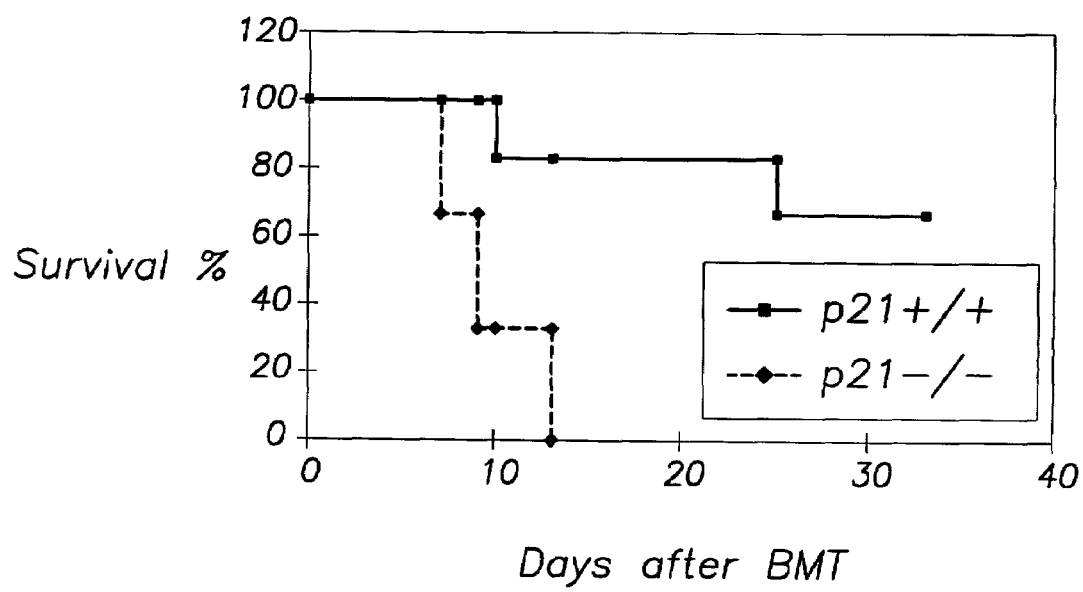
Figure 3C:
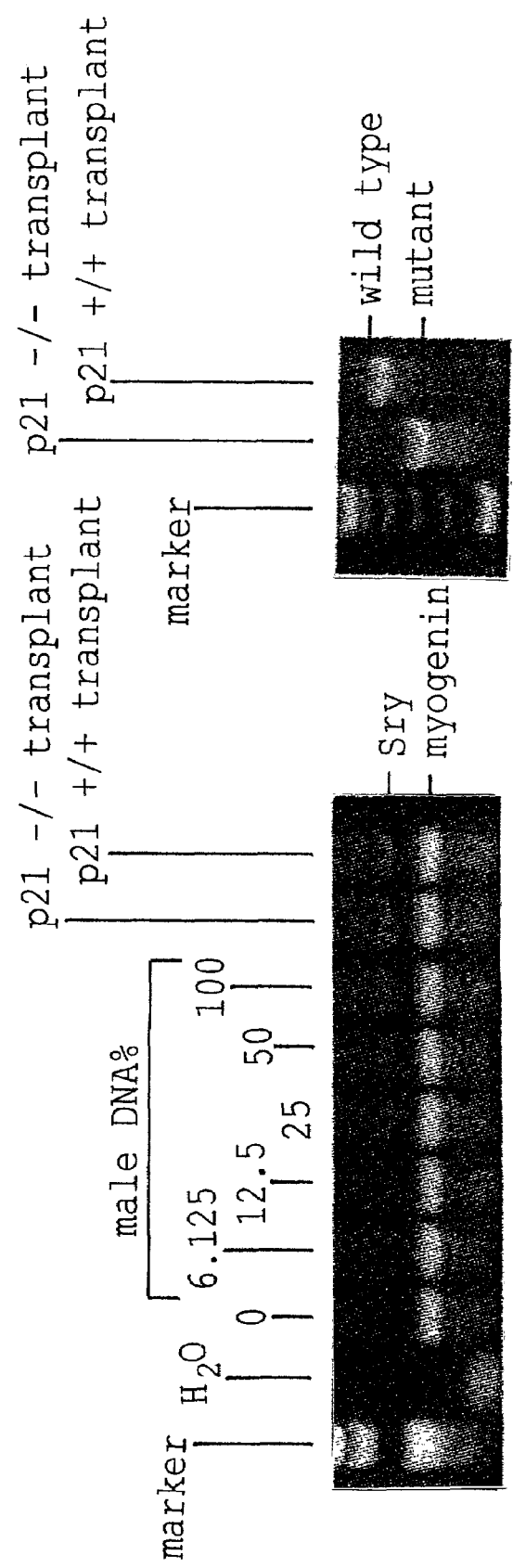

The expansion of stem cells under normal homeostatic conditions may or may not reflect a capacity to self renew under conditions of stress. The cytokine milieu dramatically changes during stress, including the elaboration of cytokine such as GM-CSF, G-CSF, or interleukin-3 with strong pro-differentiative properties. We hypothesized that the outcome of enhances proliferation of the stem cell compartment under such conditions will markedly differ from normal homeostasis and directly assesses stem cell self-renewal capacity using a serial transplantation approach (Harrison et al *J. Exp. Med.* 147:1526-1531, 1978; Harrison *Blood* 55:77-81, 1980; Harrison et al. *J. Exp. Med.* 156:1767-1779, 1982; Harrison et al. *J. Exp. Med.* 172:431-437, 1990; each of which is incorporated herein by reference). Bone marrow from ten male animals in each genotype was individually transplanted into lethally irradiated female mice. Two to four months after engraftment, 1-2×$10^6$ bone marrow cells from the transplanted recipients were used as donor cells for a lethally irradiated host and the same procedure was repeated sequentially. Recipient animals began to die after the $3^{rd}$ serial transplant and marked differential survival in the group was noted (FIG. 3a). No −/− transplanted animals survived after the 5$^{th}$ transplant whereas the +/+ transplanted animals has a 50% survival one month after the transplant. To confirm the paucity of stem cells in −/− transplanted mice, we used two different doses of cells from the 4$^{th}$ transplant to rescue lethally irradiated hosts. The two irradiation protection experiments at different doses confirmed the significantly poorer ability to rescue irradiated mice using cells from the −/− group (FIG. 3b). We observed approximately 100% contribution from the original donor p21 −/− or +/+ cells in hosts examined after each transplant by semi-quantitative Y-chromosome specific (Sry) PCR and p21 genotyping PCR (FIG. 3c).

Figure 4:
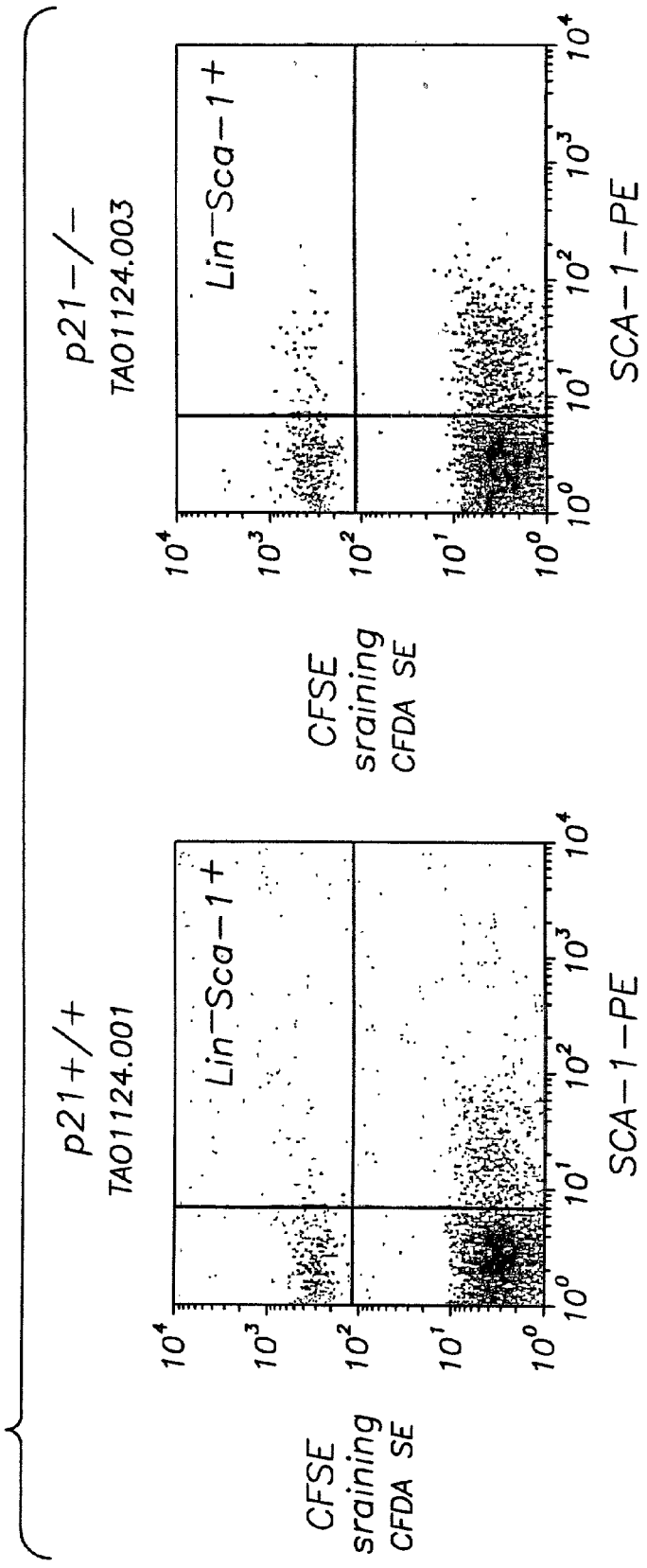
FIG. 4. p21 −/− stem cell depletion is not due to altered bone marrow homing. Donor bone marrow cells were stained with the cytoplasmic dye, CFSE, and intravenously injected into lethally irradiated mice. Bone marrow and spleen were harvested 9 hours after injection, and nucleated cells were stained with Sca-1 and lineage antibodies and analyzed by flow cytometry. 2-3 litter mates of each genotype were analyzed in each experiment. Data shown is bone marrow cells from one of two experiments with similar results.

To evaluate whether the transplantation data could be affected by altered homing of stem cells in the absence of p21, we directly measured the localization of ex vivo fluorescently labeled p21 −/− and +/+ bone marrow cells with carboxy fluorescein diacetate succinimidyl diester (CFSE) (Holyoake et al. *Blood* 94:2056-2064, 1999; incorporated herein by reference) following transplantation. The fraction of mononuclear cells or lin, Sca-1$^+$ cells homing to either bone marrow or spleen was the same for the −/− and +/+ mice (FIG. 4).

Figure 5A:
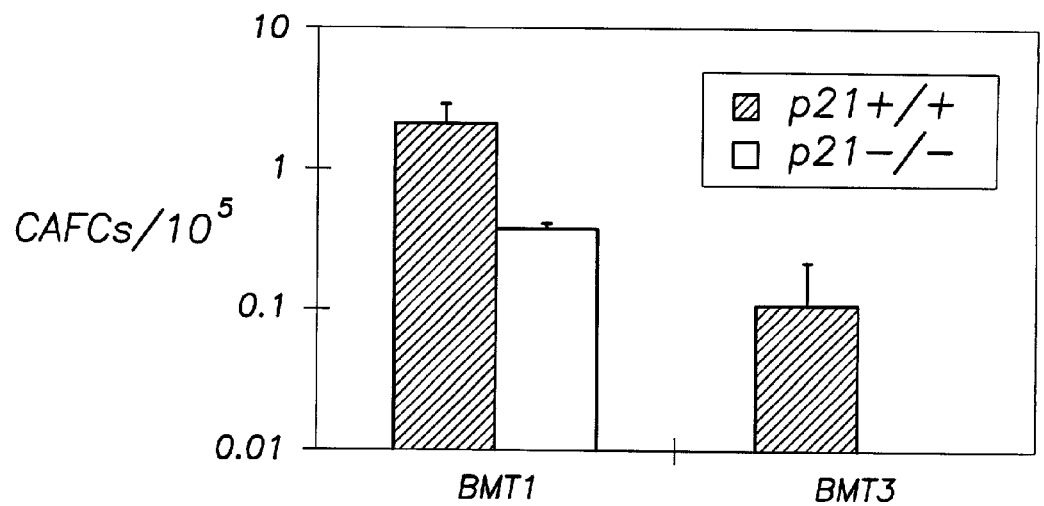
FIG. 5. CAFCs over the course of serial BMT confirm stem cell exhaustion. Long-term culture with limiting dilution was performed on the donor cells of each transplant to quantify the frequencies of hematopoietic progenitors and stem cells. Normal, not-transplanted marrow was used as a control to assure the quality of the stroma and the comparability of the experiments at different times. Data are represented as the Mean±S.D. and graphed as log scales in Y axis. All p values are less than 0.05 (−/−vs. +/+). a. CAFCs at week 5 from the $1^{st}$ and the $3^{rd}$ transplant. b. CAFCs at the indicated weeks from the $4^{th}$ transplant.
Figure 5B:
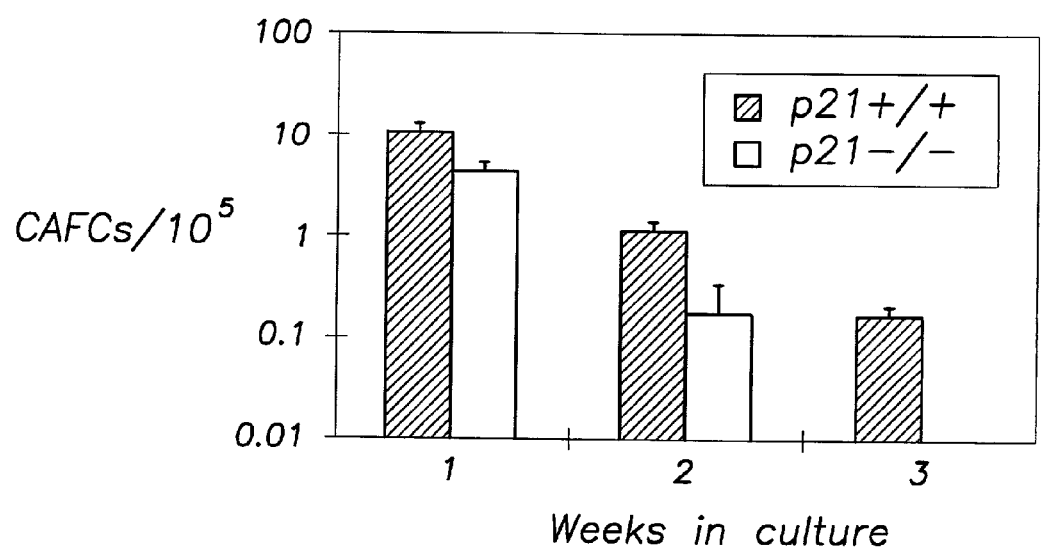

These functional in vivo parameters of stem cell function were corroborated with quantitative in vitro measures of function of the primitive cell compartment. CAFCs at week 5 from −/− mice were completely exhausted after the 3$^{rd}$ transplant while detectable CAFCs were still noted in the +/+ group (FIG. 5a). Although an absence of CAFCs after 4 weeks in both of +/+ and −/− groups from the 4$^{th}$ transplant, early cobblestones (week 2 and 3) reflecting short-term repopulating cells (Ploemacher et al. *Blood* 78:2527-2533, 1991; Ploemacher et al. *Blood* 74:2755-2763, 1989; each of which is incorporated herein by reference), demonstrated a significant difference (FIG. 5b). The CAFCs in −/− transplant recipients dampened to zero after two weeks while the CAFCs in +/+ transplant recipient remained detectable at 3 weeks. The levels of CAFCs in −/− mice were also significantly lower than in the +/+ group (all p values <0.05, FIG. 5b).

Example 2

Molecular boundary between stem and progenitor cells is marked by distinct CDKI dominance Methods Generation of homozygous mice. Heterozygote 129/B6 p27+/− mice were obtained from the laboratory of Dr. Andrew Koff (Sloan Kettering Cancer Center, New York) under the permission of the Subcommittee on Research Animal Care of the Massachusetts General Hospital (MGH). Mice were housed in sterilized microisolator cages and received autoclaved food and drinking water at the Massachusetts General Hospital animal core facility. The heterozygotes (+/−) were crossbacked into 129/sv background and bred to yield homozygous and wild-type offspring. The little mates from the same +/− parents were used in each experiment.

Mouse genotyping. Genotyping was achieved by DNA PCR. Briefly, genomic DNA was isolated from tail biopsy and analyzed by amplification using three primers (the sequences were provided by Dr. Andrew Koff): SW40 (5'-TCA AAC GTG AGA GTG TCT AAC GG3'). (SEQ ID NO. 8), SW41 (5' ACG GGC TTA TGA TTC TGA AAG TCG-3'). (SEQ ID NO. 9), and SW39 (5'-ATA TTG CTG AAG AGC TTG GCG G-3'). (SEQ ID NO. 10). SW40 is a forward primer that binds the region nt4-nt26 of pLambda-KIP-34-1. Used in conjunction with SW41, a reverse primer binding to nt209-nt186 of pLambda-KIP-34-1, this will produce a PCR product of 206 bps from the wild-type locus. SW40 used in conjunction with SW39, a forward primer binding to nt 1420-nt1441 of pMC1POLA, will produce a PCR product of 298 bps from the mutant locus. All three primers were used together in the same reaction to detect wild type and mutant loci. The conditions for thermocycling were as follows: Step 1: 94 °C., 4 min; step 2: 90° C., 30 seconds, 55° C., 30 seconds, 72 °C., 1 min, for 35 cycles; step 3: 72° C, 10 min. Diagnostic mutant and wild-type amplified bands were detected on a 2.0% agarose gel post visualization with ethidium bromide. Semi-quantitative PCR was performed using 1 µg of genomic DNA. The same primers and thermocycling parameters were applied as above except 28 cycles were performed for Step 2. The ratios of these PCR products were compared against a proportional titration curve of mutant and wild-type amplified bands (FIG. 10a).

Bone marrow sampling. Mouse bone marrow was obtained from 8-12-week-old animals from each group (−/−, +/+) sacrificed with $CO_2$. The marrow cell suspensions were flushed from femurs and tibias, filtered with 100-mesh nylon cloth (Sefar America, Inc., Kansas City, Mo.), and stored on ice until use.

Flow cytometric analysis. Flow cytometry was used to quantify the cell cycle status in the stem cell compartment. Bone marrow nucleated cells were labeled with anti-lineage antibodies [CD3, CD4, CD8, B220, Gr-1, Mac-1 (Caltac, Burlingame, Calif.), TER-119 (Pharmingen, San Diego, Calif)] and stem cell marker (Sca-1) (Pharmingen). An enriched stem cell phenotype (Sca-1$^+$Lin$^+$) and a progenitor phenotype (Sca-1$^+$Lin$^+$) were gated, and a DNA dye, To-pro-3, was used to stain the antibody-bound cells simultaneously to measure the cycling cell percentage in the populations. To measure stem cell quiescence, cells were stained with lineage antibodies, incubated with 1.67 µmol/L DNA dye, Hoechst 33342 (Hst), and 1 µg/mL RNA dye, Pyronin Y (PY), and the ratio of G0 vs. G1 was then measured in the Lin$^-$ population (Gothot et al. "Functional heterogeneity of human CD34(+) cells isolated in subcompartments of the G0/G1 phase of the cell cycle" *Blood* 90:4384-4393, 1997; incorporated herein by reference). To detect apoptotic cells, Annexin-V in conjunction with the DNA dye, 7-AAD (Fadok et al. "Exposure of phosphatidylserine on the surface of apoptotic lymphocytes triggers specific recognition and removal by macrophages" *J. Immunol.* 148:2207-2216, 1992; Shen et al. "Intrinsic human immunodeficiency virus type 1 resistance of hematopoietic stem cells despite coreceptor expression" *J. Virol.* 73:728-737, 1999; each of which is incorporated herein by reference), was used to stain Sca-1$^+$, Lin$^-$, or Lin$^+$ cells, which were then analyzed by flow cytometry. Cells excluding 7-AAD and binding Annexin-V were considered apoptotic.

Colony forming assay. Bone marrow nuclear cells were cultured in 0.8% methylcellulose, 30% fetal bovine, 1% bovine serum albumin, 0.1 mM 2-mercaptoethanol, 2.0 mM L-glutamine of α-MEM semi-solid matrix culture medium (StemCell Technologies, Inc., Vancouver, Canada) with cytokine combinations of 50 ng/ml mu-SCF (R & D System Inc., Minneapolis, Minn.), 10 ng/ml mu-IL-3 (Genzyme, Cambridge, Mass.), 10 ng/ml hu-IL-6 (Genzyme), and 3 U/ml hu-Epo (Amgen). Cells were placed at 10,000 to 20,000/200 ul/well into 48-well plates and placed at 37° C., 5% $CO_2$. After 10 days, myeloid and erythroid colonies were scored, totaled and reported as CFCs.

Long-term culture with limiting dilution. To quantify the stem cells, we adapted the cobblestone area forming cell (CAFC) assay (Ploemacher et al. "An in vitro limiting-dilution assay of long-term repopulating hematopoietic stem cells in the mouse" Blood 74:2755-2763, 1989; incorporated herein by reference) with minor modifications as follows. To prepare stromal layers, murine bone marrow nucleated cells were cultured at 33° C. in long term culture (LTC) medium [α-MEM with 12.5% house serum, 12.5% fetal bovine serum, 0.2 mM I-inositol, 20 mM folic acid, $10^{-4}$ M 2-mercaptoethanol, 2 mM L-glutamine, and $10^{-6}$ M hydrocortisone]. After 2 weeks, confluent stromal layers were trypsinized, irradiated (15 Gy), and subcultured in 96-well flat-bottomed plates at a density of $2.5 \times 10^4$/well. Cultures were then seeded with serially diluted single-cell suspensions of femoral marrow in the same medium. Marrow pooled from two to ten animals of each type was seeded at 2-fold dilutions ($10^5$–1562 cells/well) for nucleated bone marrow cells. Cultures were very gently re-fed with 50:1 medium after semi-depletion weekly and the CAFCs and/or blast colonies (Ploemacher et al. "Use of limiting-dilution type long-term marrow cultures in frequency analysis of marrow-repopulating and spleen colony-forming hematopoietic stem cells in the mouse" Blood 78:2527-2533, 1991; Muller-Sieburg et al. "Genetic control of the frequency of hematopoietic stem cells in mice: mapping of a candidate locus to chromosome 1" J. Exp. Med. 183:1141-1150, 1996; each of which is incorporated herein by reference) were scored until the $6^{th}$ week. To measure LIC-IC, methylcellulose medium for CFC (see above) was overlaid into the wells at week 5 and the colonies were counted at day 10. A limiting dilution software ("Maxrob", provided by Julian Down, BioTranspant Inc.) was used to calculate the frequency of CAFC or LTC-IC.

5-FU exposure in vivo. The anti-metabolite, 5-FU, was used to functionally test the cycling status of primitive hematopoietic cells in vivo. A single injection of 5-FU i.v. at a dose of 200 mg/kg was administered and cells for long-term culture with limiting dilution and colony forming assay were obtained one day after the injection.

Serial bone marrow transplantation. Serial bone marrow transplantation (Harrison "Competitive repopulation: a new assay for long-term stem cell functional capacity" Blood 55:77-81, 1980; Harrison et al. "Loss of proliferative capacity in immunohemopoietic stem cells caused by serial transplantation rather than aging" J Exp. Med 147:1526-1531, 1978; Harrison et al. "Effects of transplantation on the primitive immunohematopoietic stem cell" J Exp. Med. 172:431-437, 1990; each of which is incorporated herein by reference) was used to evaluate the ability of stem cells to self-renew. Male mice (8-12 weeks old) were used as marrow donors and the marrow cells prepared as above. Female recipient mice (8-10 weeks old, 129/SV, Jackson laboratory) were lethally irradiated using a Mark 1-Model 25 $^{137}$Cesium Irradiator (JL Shepherd and Associates, San Fernando, Calif.) with 10 Gy whole body irradiation (WBI) at 5.96 Gy/min. One to two million nucleated cells in 1 ml 199 Medium were injected intravenously through 27 gauge needles into the lateral tail veins of warmed recipients. Recipient mice were monitored daily for survival until next transplant. The mice were sacrificed at 1-4 months and bone marrow cells were prepared from those sacrificed mice and injected into new female recipients. This process was repeated for 4 sequential transplants with survival frequency plotted for each group. Long-term culture with limiting dilution and colony forming assays described above were performed on the donor cells of each transplant to quantify the frequencies of stem and progenitor cells.

Short-term radiation-protection assay. $10^5$ marrow nucleated cells from the fourth transplant were transplanted into lethally irradiated female mice as described above, and animal survival frequency was plotted for each group after 30 days. Results were analyzed using a log-rank nonparametric test and expressed as Kaplan-Meier survival curves.

Competitive long-term repopulation. Equal numbers of bone marrow nucleated cells from p27 +/+ and p27 −/− mice were mixed and transplanted into the lethally irradiated recipients as described in the serial transplantation section. Blood was collected at 6 and 9 months for semi-quantitative p27 PCR analysis. After 12 months, mice were sacrificed and bone marrow nucleated cells were prepared for PCR analysis and hematopoietic cell culture (CFC, CAFC and LTC-IC; see the CFC and long-term culture sections). Individual colonies from the CFC culture or individual CAFC/LTC-ICs from different wells were isolated by micropipette and analyzed by PCR for p27.

Results

Mice Engineered to be p27 −/− Have a Normal Stem Cell Pool, but an Enlarged Progenitor Cell Pool We first assessed the impact of p27 deletion on different hematopoietic cell compartments by quantifying the functional populations of progenitor cells (using methylcellulose colony-forming cell (CFC) assays and of more primitive cells (using long-term cobblestone area-forming cell (CAFC) assay) (Ploemacher et al. "An in vitro limiting-dilution assay of long-term repopulating hematopoietic stem cells in the mouse" Blood 74:2755-2763, 1989; Ploemacher et al. "Use of limiting-dilution type long-term marrow cultures in frequency analysis of marrow-repopulating and spleen colony-forming hematopoietic stem cells in the mouse" Blood 78:2527-2533, 1991; each of which is incorporated herein by reference). The latter assays linearly correlate with in vivo repopulating potential and were used here as a functional stem cell assay.

Figures 6A, 6B:
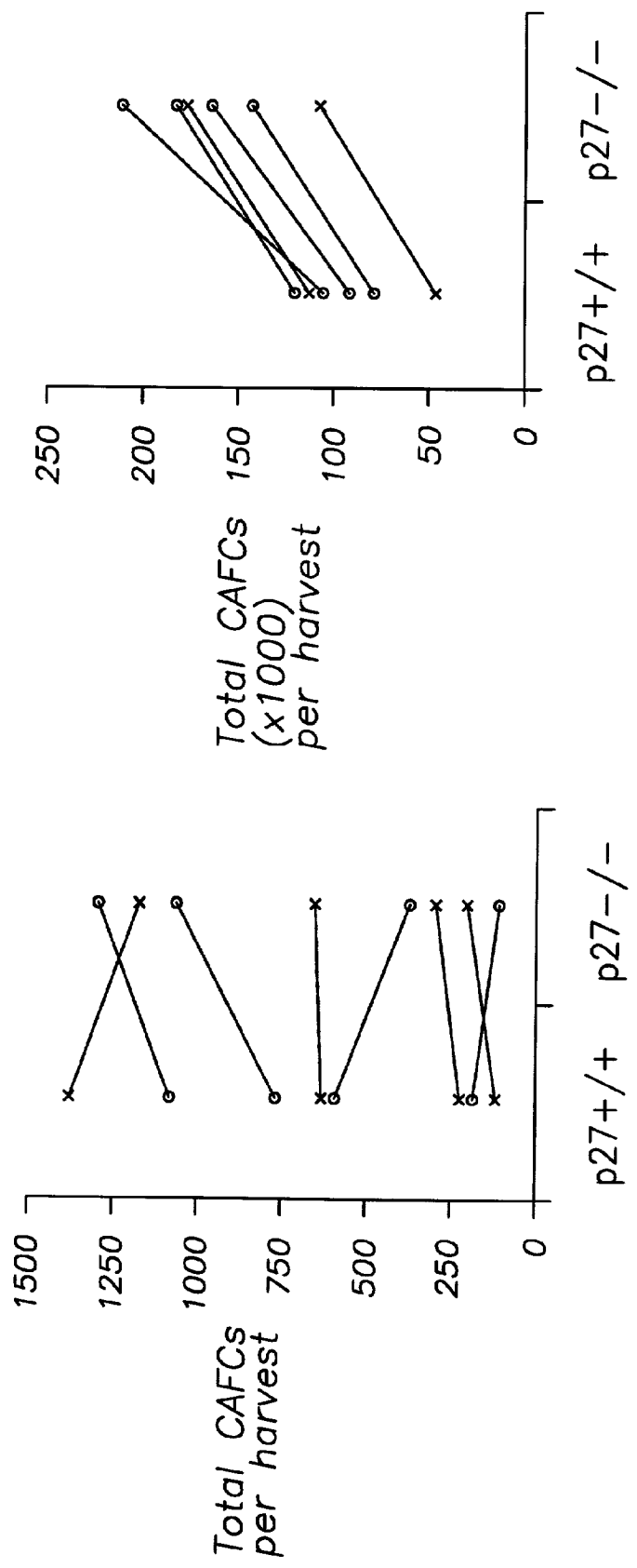
FIG. 6. The long-term culture and colony forming assays demonstrate an unchanged stem cell pool size and an enlarged progenitor pool in the p27 −/− mice. (a) comparison of CAFCs scored at week 5 between p27 +/+ and −/− mice (per harvest of two femurs). Each data point was generated from three to five limiting dilutions. Each pair was pooled from two to three −/− or +/+ littermate mice in each experiment. Data were analyzed using the paired t-test (P=0.3861, n=7). (b) Comparison of CFCs between p27 +/+ and −/− mice (per harvest of two femurs). Data represent colony-forming ability at day 10. Each pair was pooled from two to three −/− or +/+ littermate mice in each experiment. Each data point was generated from four replicates, and data were analyzed using the paired t-test (P−0.0006, n−5). Each line shows one data pair from the same experiment, and the bold thicker line shows the average value from all the independent experiments.

We observed a marked contrast between p27 −/− mice and p21 −/− mice. In the p21 −/− animals, stem cell populations were doubled and progenitor populations unchanged in previous studies (Cheng et al. "Hematopoietic stem cell quiescence maintained by p21 (cip1/waf1)" Science 287:1804-1808, 2000; Mantel et al. "Involvement of p21cip-1 and p27kip-1 in the molecular mechanisms of steel factor-induced proliferative synergy in vitro and of p21cip-1 in the maintenance of stem/progenitor cells in vivo" Blood 88:3710-3719, 1996; each of which is incorporated herein by reference), whereas p27 −/− animals had an increase in progenitors but no change in stem cell numbers. Decreased numbers of CAFC per nucleated cell in the p27 −/− animals were noted compared to +/+ animals (33% reduction of CAFC frequency in −/− animals, n=7, p=0.0391). However, normalization of the values for the overall increase in marrow cellularity (Table 5) in the p27 −/− mouse (4.40 vs, $2.83 \times 10^7$/femur pair; p=0.0072; n=6) indicated that the number of stem cells per hematopoietic organ (2 femurs/harvest) was not significantly different from the +/+ control (p=0.3861, n=7) (FIG. 6a). However, the progenitor population was significantly different, with an increased CFC population in p27 −/− versus +/+ animals (p=0.0006, n=5) (FIG. 6b). Therefore, a disproportionate increase in progenitor populations and overall cellularity diluted the stem cell fraction, but the absolute number of stem cells was unchanged from control.

TABLE 5

Comparison of total cell number per bone marrow harvest indicates a higher marrow cellularity in the p27 −/− mice

| Experiment # | p27 +/+ | p27 −/− |
|---|---|---|
| 1 | 3.86 | 4.26 |
| 2 | 1.63 | 3.03 |
| 3 | 2.2 | 3.2 |
| 4 | 3.89 | 6.9 |
| 5 | 2 | 2.91 |
| 6 | 3.4 | 6.07 |
| Mean | 2.83 | 4.40 |
| p value | 0.0072 | |

Each data point represents the mean from 1-3 −/− or +/+ littermate mice in each experiment.
Total cell number (× $10^7$/femur pair) was counted from each harvest and data were analyzed using the paired t-test.

An Altered Cell Cycle Profile of Progenitor Cells, but Not Stem Cells In the Absence of P27

Figures 1, 7A:
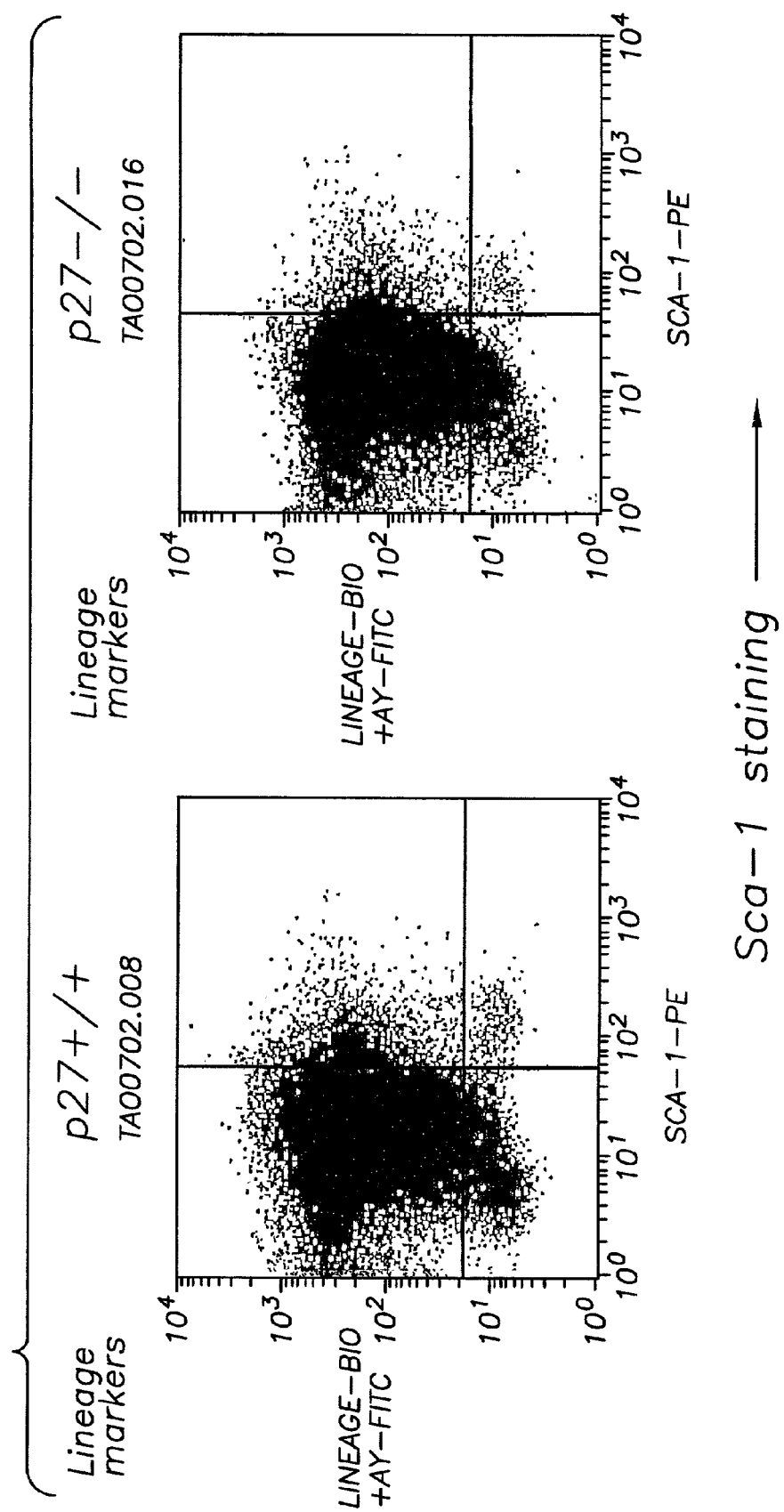
Figure 7A:
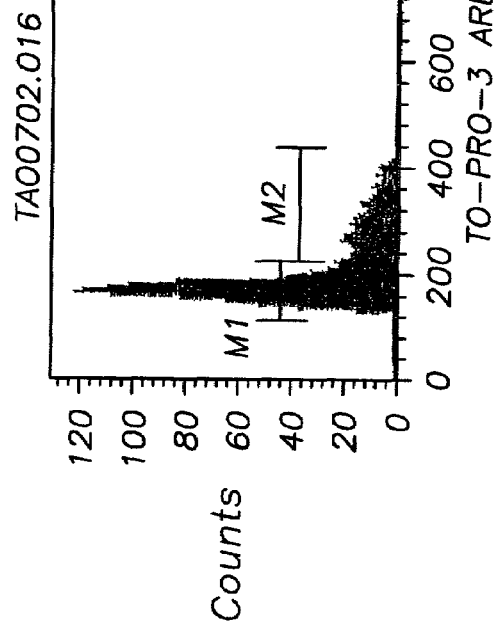
FIG. 7. Altered cell cycle profile of progenitor cells, but not stem cells, in the p27 −/− marrow. Mouse bone marrow cells were stained with lineage antibodies and stem cell marker (Sca-1) to separate the enriched stem (Sca-1$^+$Lin$^+$) and progenitor (Sca-1$^+$Lin$^+$) pools (a, upper panel). Simultaneous staining with the DNA dye, To-pro-3, was used to determine the percentage of S+G2/M cells in each population (a, middle and lower panels). Data from multiple experiments are summarized in (b) (*P=0.0215, n=7 in Sca-1$^+$Lin$^+$ cells; P=0.3591, n=9 in Sca-1$^+$Lin cells). To determine the ratio of G0 to G1 in stem cell population, the RNA dye (pyronin Y, PY) and DNA dye (Hoechst 33342) were used instead of To-pro-3, and the percentage of G0 (py$^{low}$) was obtained in the G0/G1 fraction (Hoechst$^{low}$Lin) 4,28 shown in (c) (P=0.1591, n=7). Each data point represents the mean from one to three −/−or +/+ littermate mice in each experiment. Data were analyzed using the paired t-test.
Figure 2:
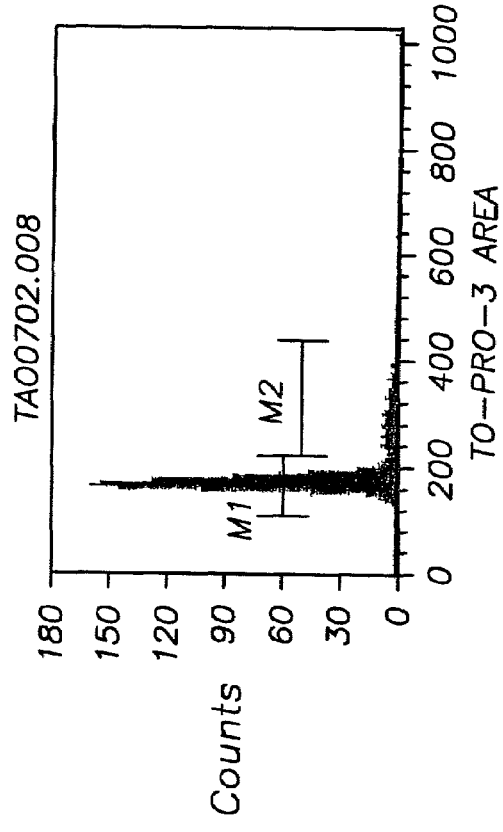
Figure 7A:
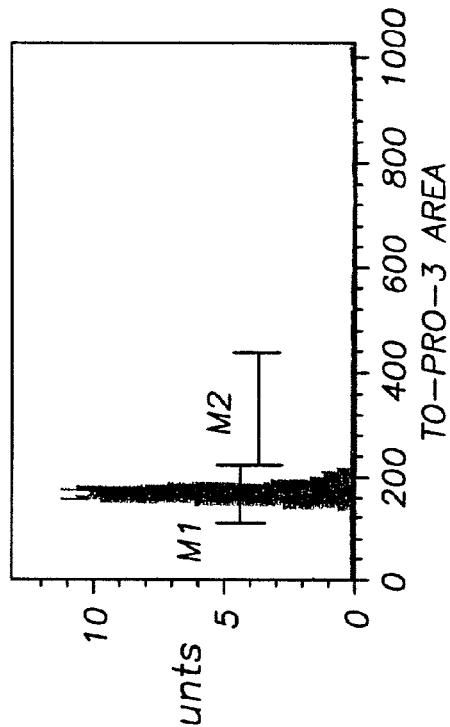
Figure 3:
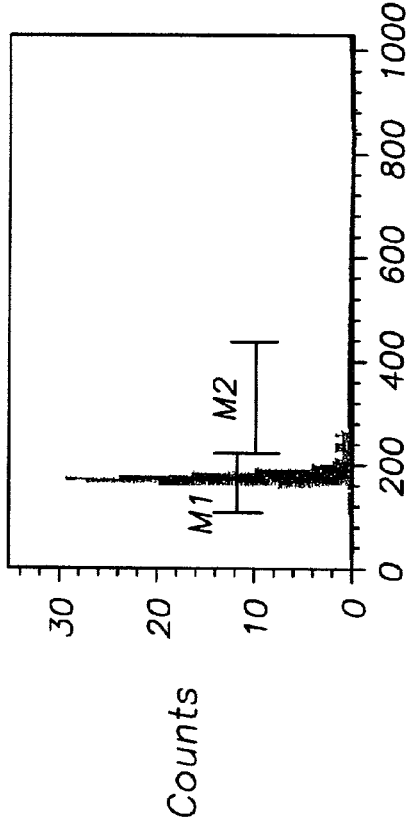
Figure 7B:
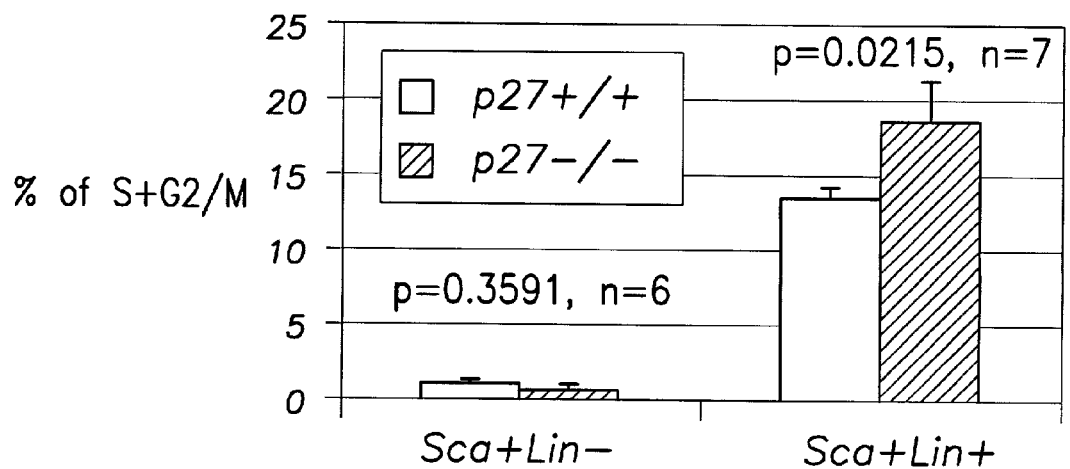
Figure 7C:
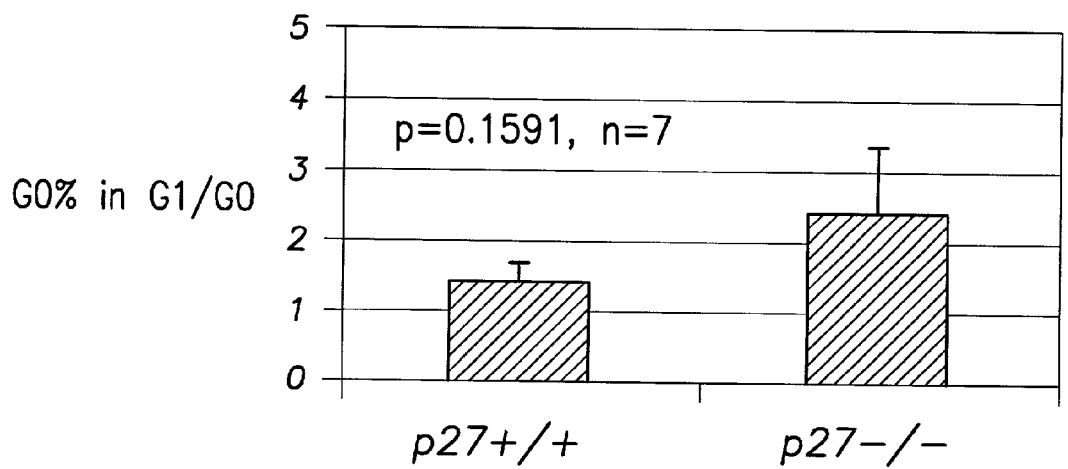

To directly measure cell cycle parameters of primitive cell populations in the p27 +/+ and −/− animals, flow cytometric analysis was performed. Because hematopoietic stem cells have been shown to be positive for the stem cell marker Sca-1 and negative for lineage markers (Spangrude et al. "Purification and characterization of mouse hematopoietic stems cells [published erratum appears in Science 1989 Jun. 2; 244(4908):1030]" Science 241:58-62, 1988; incorporated herein by reference), we reasoned that lineage marker-expressing cells in the Sca-1+ population reflected a population of maturing lineage-committed progenitors. We confirmed this by testing for CAFC and detected a decrease of 9-20 times in Lin$^+$Sca-1$^+$ cells compared to Lin$^{-Sca-}$1$^+$ cells. Therefore, flow cytometry was used to separate the enriched stem cell (Sca-1$^+$Lin$^-$)and progenitor cell (Sca-1$^+$Lin$^-$) pools from marrow nucleated cells and the cell cycle status (S+G2/M percentage) was analyzed by simultaneously staining with the DNA dye, To-pro-3. We observed a similar S+G2/M percentage of Sca-1$^+$Lin$^-$ in the p27 +/+ and −/− animals (p=0.3591, n=6), but a higher S+G2/M percentage of Sca-1$^+$Lin$^+$ in the p27 −/− animals (FIG. 7a and 7b, p=0.0215, n=7). To further distinguish a quiescent fraction (G0) versus G1 in the stem cell pool, an RNA dye, Pyronin Y, was used to stain the marrow nucleated cells within a stringent gate of Lin$^-$ cells in conjunction with a DNA dye, Hoechst 33342 (Cheng et al. "Hematopoietic stem cell quiescence maintained by p21 (cip1/waf1) " Science 287:1804-1808, 2000; Gothot et al. "Functional heterogeneity of human CD34(+) cells isolated in subcompartments of the G0/G1 phase of the cell cycle"Blood 90:4384-4393, 1997; each of which is incorporated herein by reference). No difference was observed between p27 −/− and +/+ cells (FIG. 7c) unlike the p21 −/− stem cells in which a significantly lower fraction of quiescent (G0) cells had been previously found (Cheng et al. "Hematopoietic stem cell quiescence maintained by p21 (cip1/waf1)" Science 287:1804-1808, 2000; incorporated herein by reference). These data indicate an unperturbed cell cycle status of stem cells, but an increased fraction of progenitor cells in active cycle in the absence of p27.

Figure 8:
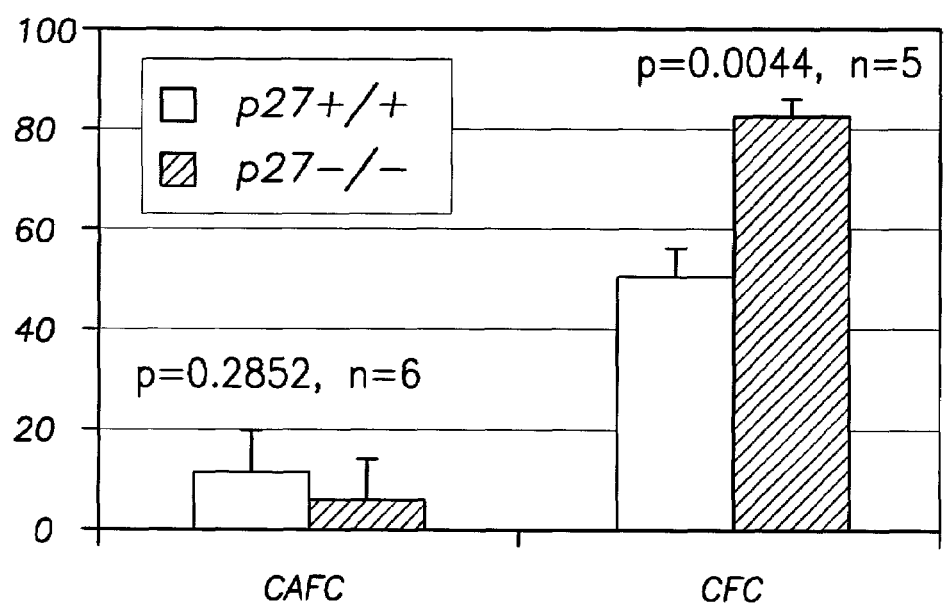
FIG. 8. Treatment with 5-FU in vivo demonstrates more active cell cycling in the progenitor pool, but not in the stem cell pool of the p27 −/−mice. One day after a single intravenous injection of 5-FU at the dose of 200 mg/kg was given, cells for long-term culture with limiting dilution and colony forming ability were obtained. CAFCs were counted at week 5, and CFCs were counted at day 10. y-axis values=[(CAFCs or CFCs from untreated mice− CAFCs or CFCs from 5-FU treated mice)/CAFCs or CFCs from un-treated mice]×100%. Data represent the mean from multiple independent experiments. Three littermates for each genotype were used in each experiment, and three to five limiting dilutions were used for each sample in the long-term culture. The Student's t-test was used for comparative analysis: *P=0.0044, n=5 for CFC and P=0.2852, n=6 for CAFC, comparing p27 −/− (black bars) with p27 +/+ (white bars) cells.

Functional evaluation of cell cycle status was performed by exposing animals to the cell cycle-dependent anti-metabolite 5-fluorouracil (5-FU), which selectively kills cycling cells (Lerner et al. "5-Fluorouracil spares hematopoietic stem cells responsible for long-term repopulation" Exp. Hematol. 18:114-118, 1990; Berardi et al. "Functional isolation and characterization of human hematopoietic stem cells" Science 267:104-108, 1995; each of which is incorporated herein by reference). Littermate −/− or +/+ mice were injected with 200 mg/kg of 5-FU or phosphate-buffered saline alone; marrow was harvested one day later, and long-term co-culture (CAFC) and colony forming cell (CFC) assays performed (FIG. 8). No difference in the yield of CAFC was noted between +/+ or −/− animals suggesting similar proliferative kinetics in the primitive or stem cell compartment (p=0.2852, n=6). However, a significant reduction of CFC was observed in the p27 −/− group compared to the +/+ group controls (82.7% versus 50.6%, p=0.0044, n=5) (FIG. 8). The proliferative fraction of cells in the progenitor pool was therefore larger in those animals lacking p27, providing a basis for the expanded size of the progenitor cell population.

An Unchanged Apoptotic Fraction of Hematopoietic Cells in the Absence of p27

Under homeostatic conditions, an enlarged cell population in vivo may be caused by increased cell proliferation, decreased cell death, or both. To assess whether or not altered apoptosis contributed to the expanded progenitor compartment, we evaluated cells by Annexin-V staining (Fadok et al. "Exposure of phosphatidylserine on the surface of apoptotic lymphocytes triggers specific recognition and removal by macrophages" J. Immunol. 148:2207-2216, 1992; incorporated herein by reference) and could detect no difference in apoptosis in either the Sca-1$^+$ Lin$^-$ stem cell pool or Sca-1$^+$ Lin$^+$ progenitor cells between p27 −/− and +/+ littermate control mice (mean 2.5±0.8 vs. 2.5±0.8 and 7.3±2.5 vs. 7.2±2.2, respectively; n=4) (Table 6)

TABLE 6

The expansion of progenitor cells in the p27 −/− mice is not due to altered apoptotic effect

| | Sca-1$^+$Lin$^-$ | | Sca-1$^+$Lin$^+$ | |
|---|---|---|---|---|
| Experiment # | p27 +/+ | p27 −/− | p27 +/+ | p27 −/− |
| 1 | 2.32 | 3.27 | 4.27 | 6.77 |
| 2 | 3.47 | 1.38 | 6.27 | 4.81 |
| 3 | 2.76 | 2.87 | 9.66 | 10.1 |
| 4 | 1.62 | 2.28 | 9 | 6.94 |
| Mean | 2.5425 | 2.45 | 7.3 | 7.155 |
| SD | 0.776332 | 0.821097 | 2.496758 | 2.18834 |

Bone marrow nucleated cells were stained with Sca-1, lineage antibodies, DNA dye (7-AAD) and the apoptosis marker (Annexin-V) for flow analysis. The percentage of apoptotic cells (Annexin-V$^+$, 7$^-$AAD-) is listed here. 2-3 littermates of each genotype were analyzed in each experiment.

Figure 9A:
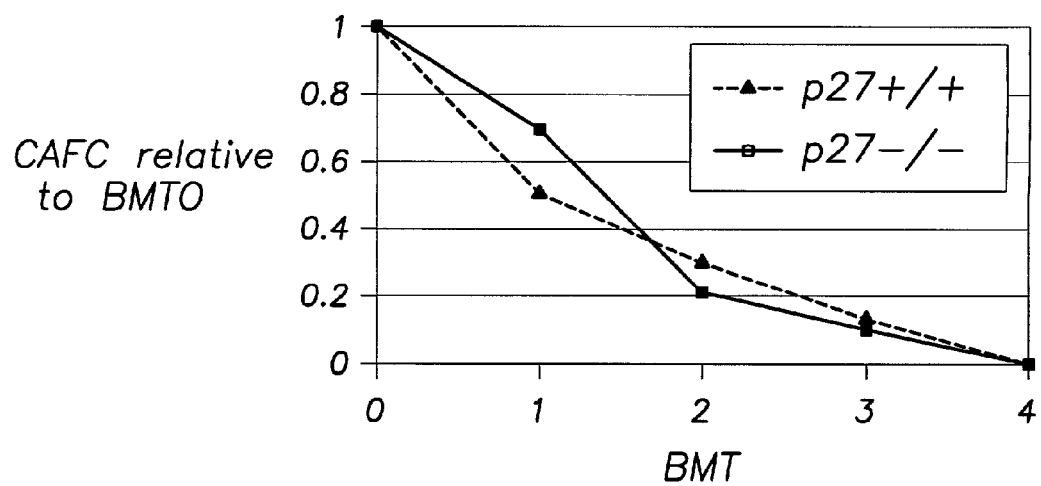
FIG. 9. Serial bone marrow transplantation (BMT) demonstrates an unaltered self-renewal of hematopoietic stem cells and an enhanced activity of progenitor cells in the p27 −/− transplanted mice. Male mice were used as marrow donors. Female recipient mice were lethally irradiated with 10 Gy whole-body irradiation at 5.96 Gy/min. Two million nucleated cells were injected intravenously into the lateral tail veins of warmed recipients. Recipient mice were monitored daily for survival for more than one month. The mice were euthanized after one to four months, and bone marrow cells were prepared from those euthanized and injected into new female irradiated recipients. This process was repeated four more times. a. CAFC decline (relative to pre-BMT sample) over the course of serial BMT. The donor cells of each transplant were subjected to long-term culture with limiting dilution to quantify the frequencies of stem cells. Normal, not-transplanted marrow was used as a control to assure the quality of the stroma and the comparability of the experiments at different times. There was no significant difference between the p27 −/− (solid line) and p27 +/+ (dotted line) groups. b. CFC activities during serial BMT indicate expansion of progenitor pools in the p27 −/− transplanted mice. The Student's t-test was used for analysis: *P=0.001 in the third BMT and P>0.05 in other BMTs between p27 −/− (black bars) and p27+/+ (white bars) cells. c. Short-term radiation protection of the marrow from the 4$^{th}$ transplant. $10^5$ cells from the fourth BMT mice were transplanted into the lethally irradiated recipients described as above, and survival data were analyzed using a log-rank nonparametric test (P=0.036, n=10 in the p27 −/− group (solid line) or n=9 in the p27 +/+ group (dotted line)) and expressed as Kaplan-Meier survival curves.

Reasoning that steady state of the stem cell compartment may be unperturbed yet other physiologic functions affected under stress, sequential bone marrow transplant was performed. Bone marrow from p27 +/+ or −/− male animals in each genotype was transplanted into 10 lethally irradiated female mice. One to four months after engraftment, 1-2×10$^6$ bone marrow cells from the transplanted recipients were used as donor cells for a lethally irradiated host and the same procedure was repeated sequentially. Chimerism was determined as ~100% donor derived after each transplant by semi-quantitative Y chromosome-specific (Sry) PCR (Muller et al. "ES cells have only a limited lymphopoietic potential after adoptive transfer into mouse recipients"Development 118: 1343-1351, 1993; incorporated herein by reference) and p27 genotyping PCR (data not shown). There was no difference in bone marrow homing among p27 −/− stem cells compared with +/+ controls as assessed by carboxyfluorescein diacetate succinimidyl diester (CFSE) (Weston et al. "New fluorescent dyes for lymphocyte migration studies. Analysis by flow cytometry and fluorescence microscopy" J. Immunol. Methods 133:87-97, 1990; Grzegorzewski et al. "Recombinant transforming growth factor beta 1 and beta 2 protect mice form acutely lethal doses of 5-fluorouracil and doxorubicin" *J. Exp. Med.* 180:1047-1057, 1994; incorporated herein by reference) staining of Sca-1$^+$Lin$^-$ cells (data not shown). Stem cell quantitation was performed by CAFC analysis following each transplantation. A comparable decay rate in CAFC was noted in each group, indicating that stem cell renewal was equivalent in the p27 −/− and +/+ animals (FIG. 9a).

Figure 9B:
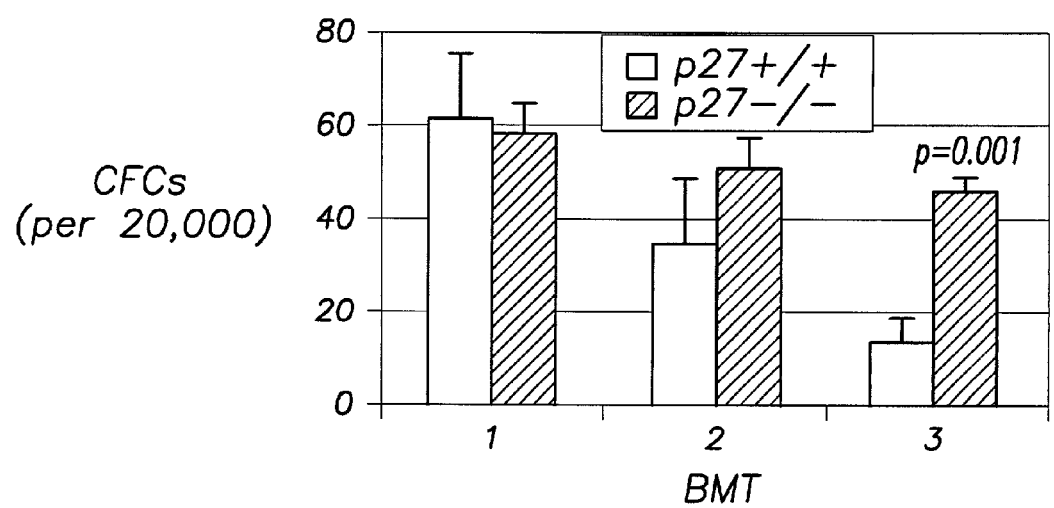
Figure 9C:
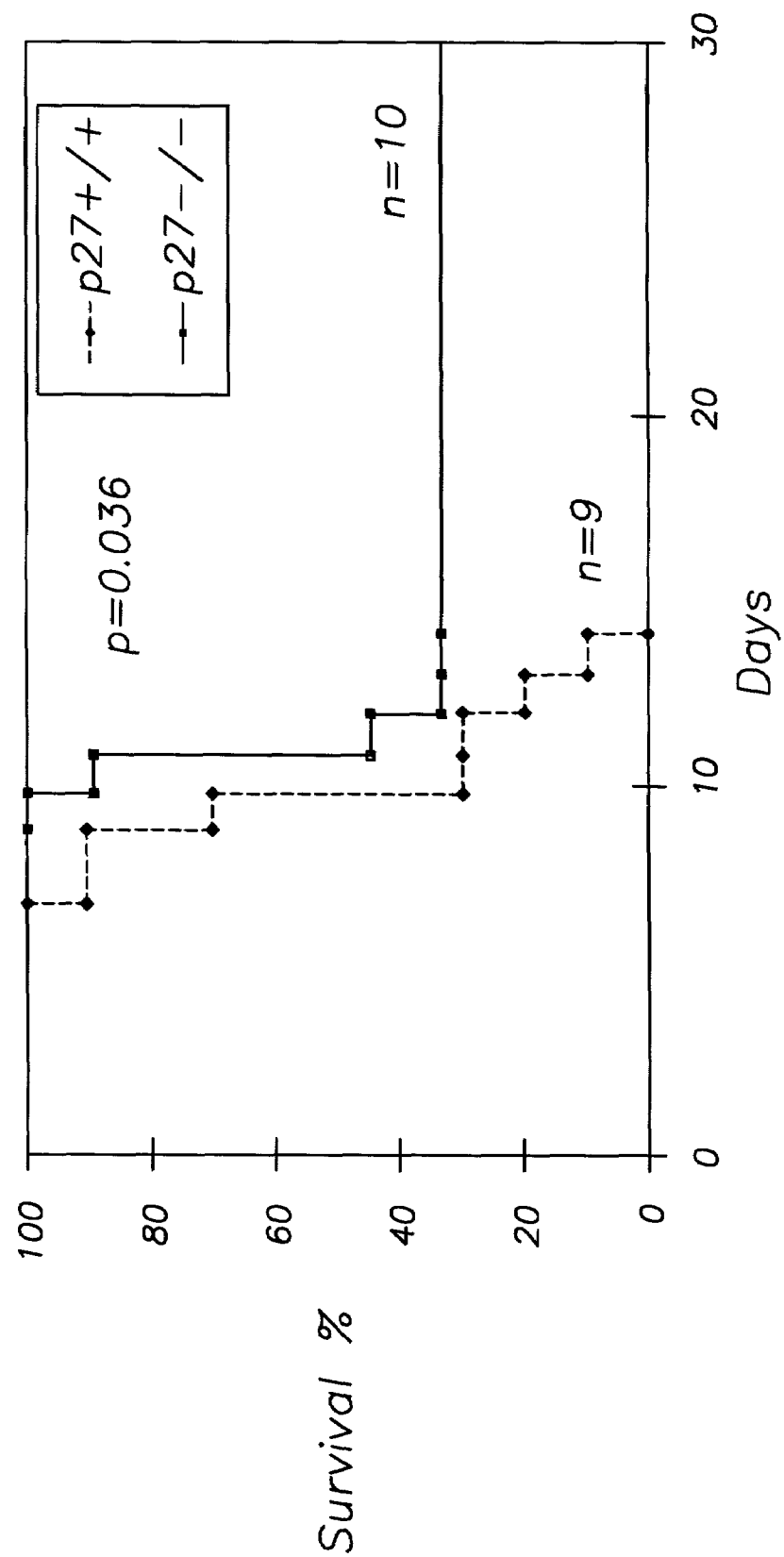

Interestingly, however, the progenitor cell pool from the p27 −/− animals was capable of expansion and relative regeneration after serial transplantation when wild-type progenitors were markedly depleted (FIG. 9b). Furthermore, the functional capacity of these cells was evident in improved animal survival in a short-term radiation-protection assay (FIG. 9c), even after the fourth serial transplant when stem cells were no longer detectable. These data demonstrate markedly altered cell kinetics among progenitors, but not stem cells, in the absence of p27. This contrasts dramatically with the increased stem cell pool and unaffected progenitor population in the p21 −/− setting (Cheng et al. "Hematopoietic stem cell quiescence maintained by p21 (cip1/waf1)" *Science* 287:1804-1808, 2000; each of which is incorporated herein by reference).

Preferential Outgrowth of p27 −/− Stem Cell Descendent Cells Following Long-Term Engraftment We next tested the role of p27 and thereby the role of progenitor cell cycle inhibition in the context of long-term engraftment. We performed a competitive transplantation in which −/− and +/+ bone marrow nucleated cells were admixed 1:1 and transplanted into an irradiated wild-type recipient. It should again be noted that the representation of stem cells in the −/− nucleated cell preparations is proportionately lower than in +/+ controls. The admixture of the stem cell population is therefore uneven, with 40% derived from −/− marrow. After transplantation, semiquantitative PCR of p27 was used to monitor each genotype in populations of bone marrow and blood cells over a one-year interval. It has been shown in other settings that the proportion of stem cells from a normal host is reflected in a similar proportion of total bone marrow cells and blood cells (Harrison "Competitive repopulation: a new assay for long-term stem cell functional capacity" *Blood* 55:77-81, 1980; Szilvassy et al. "Quantitative assay for totipotent reconstituting hematopoietic stem cells by a competitive repopulation strategy" *Proc. Natl. Acad. Sci. USA* 87:8736-8740, 1990; each of which is incorporated herein by reference). This is the basis for the competitive repopulation experiments performed in congenic mice as a tool for measuring stem cell populations. However, in the context of altered cell cycle regulation by p27 deficiency, proportionate representation in various cellular compartments was strikingly altered.

Figure 10D:
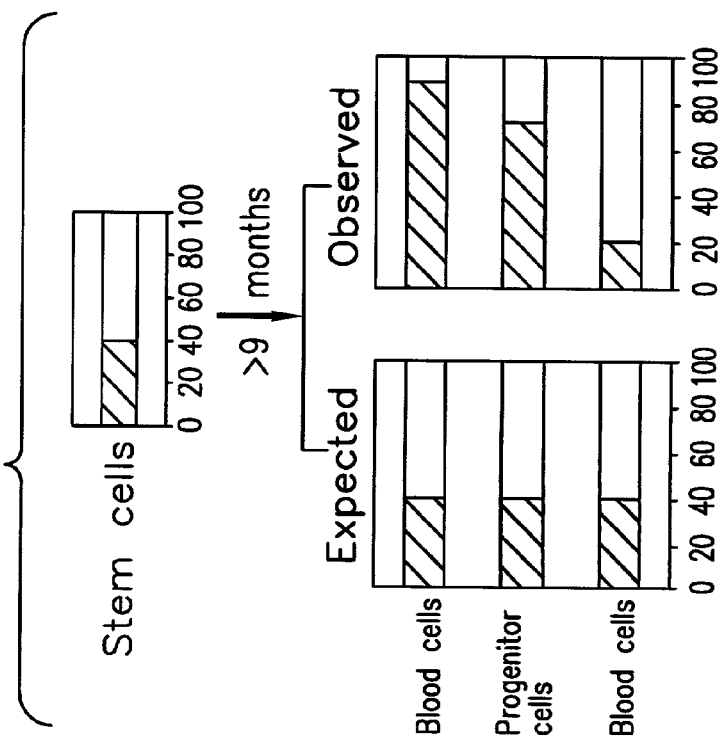
FIG. 10. Competitive repopulation assay demonstrates preferential outgrowth of p27 −/− progenitor and mature cells following long-term engraftment. Equal numbers of bone marrow nucleated cells from p27 +/+ and p27 −/− mice (five mice for each genotype) were mixed and transplanted into five lethally irradiated recipients. Blood was collected at 6, 9, and 11 months for semiquantitative p27 genotyping PCR analysis. (a). At 11-12 months, mice were sacrificed and bone marrow nucleated cells were prepared for PCR analysis (b) and hematopoietic cell culture. Individual colonies from CFC culture or individual CAFC and LTC-ICs from different wells were harvested and analyzed by PCR for p27 to determine the distribution of p27 −/− (black bars) or p27 +/+ (white bars) in the indicated compartment (c). (d) Overall observed results from this study compared with the conventionally expected result: p27 −/− (black bars); p27 +/+ (white bars).
Figure 10C:
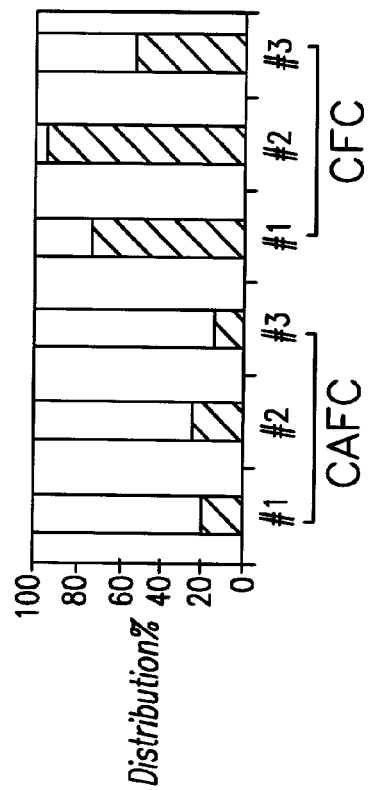

Even though the fraction of −/− stem cells transplanted was approximately 40%, after six months the fraction of p27 −/− cells in the blood reached levels of ~80% and was sustained at elevated levels (FIG. 10a). In addition, the fraction of −/− marrow nucleated cells (predominately a progenitor cell population and its descendents) was >80% at the time of euthanasia at 11 or 12 months (FIG. 10b). CAFC, LTC-IC, and CFC analyses were performed on the marrow specimens. Individual CAFC, LTC-IC, or CFC were then isolated by micropipette for PCR analysis of the p27 genotype. The data confirmed that the proportion of genotypically −/− cells in the CAFC, LTC-IC, or stem cell population was comparable to or less than what was transplanted. In contrast, the CFC or progenitor cell population demonstrated a relative overrepresentation of the −/− genotype (FIG. 10c). The fraction of stem cells transplanted thereby disproportionately contributed to progenitor cell population, which in turn disproportionately contributed to the blood cell population in the absence of p27. Feedback governing cell pool size therefore is skewed in the absence of p27, permitting overgrowth of progenitors and their descendents in a competitive situation (FIG. 10d).

Discussion

These data support highly differentiation stage-specific regulatory roles for distinct members of the CDKI Cip/Kip family (Table 7).

TABLE 7

Distinct impact of p21 and p27 on hematopoiesis

|  | p21 −/− | p27 −/− |
| --- | --- | --- |
| Stem cells | Increased number<br>Increased cycling<br>Accelerated exhaustion under stress | Normal number<br>Normal cycling<br>Normal exhaustion under stress |
| Progenitor cells | Normal number<br>Normal to decreased cycling<br>Not able to compensate for stem cell exhaustion post transplant | Increased number<br>Increased cycling<br>Outcompeted +/+ progenitors in hemeostasis and enhanced protection post transplant |

Each phenotype change is based on the relative alteration compared with wild type, littermate controls in this and other studies.

The clearly delineated and apparently exclusive dominance of p27 in progenitor cells and p21 in stem cells demarcates a molecular boundary that is unique as far as we know. Cytokine receptors (Berardi et al. "Functional isolation and characterization of human hematopoietic stem cells" *Science* 267:104-108, 1995; incorporated herein by reference), chemokine receptors (Shen et al. "Intrinsic human immunodeficiency virus type 1 resistance of hematopoietic stem cells despite coreceptor expression" *J. Virol.* 73:728-737, 1999; incorporated herein by reference), adhesion molecules (Becker et al. "Adhesion receptor expression by hematopoietic cell lines and murine progenitors: modulation by cytokines and cell cycle status" *Exp. Hematol.* 27:533-541, 1999; Roy et al. "Expression and function of cell adhesion molecules on fetal liver, cord blood and bone marrow hematopoietic progenitors: implication of anatomical localization and developmental stage specific regulation of hematopoiesis" *Exp. Hematol.* 27:302-312, 1999; incorporated herein by reference), and transcription factors (Cheng et al. "Temporal mapping of gene expression levels during the differentiation of individual primary hematopoietic cells" *Proc. Natl. Acad. Sci. USA* 93:13158-13163, 1996; Shivdasani et al. "The transcriptional control of hematopoiesis [see comments]" *Blood* 87:4025-4039, 1996; Tenen et al. "Transcription factors, normal myeloid development, and leukemia" *Blood* 90:489-519, 1997; Test et al. "Expression of growth factor receptors in unilineage differentiation culture of purified hematopoietic progenitors" *Blood* 88:3391-3406, 1996; each of which is incorporated herein by reference) have been shown to be expressed in overlapping populations of precursor populations. Whereas other regulatory molecules may contribute to the differential sensitivity of stem cells and progenitors to proliferative signals, cell cycle control is highly divergent at the level of the G1-S checkpoint. The distinction between the participating CDKIs may explain in part the highly dichotomous proliferative capability of stem cells as compared to progenitor cells that characterize the hematopoietic and other differentiation systems. Additionally, it provides specific targets for selective manipulation of stem cell versus progenitor cell compartments. To the extent that hematopoiesis mimics other stem and progenitor populations in tissue development, this distinction may point to useful strategies for altering specific precursor pools in size and activity.

The observation that competition between p27 −/− and +/+ cells results in overrepresentation of the −/− progenitor and blood cells indicates the critical function of inhibition in dictating homeostasis in the later phases of hematopoiesis. The importance of pro-proliferative cues for hematopoiesis has been demonstrated (Carver-Moore et al. "Low levels of erythroid and myeloid progenitors in thrombopoietin-and-c-mpl-deficient mice" *Blood* 88:803-808, 1996; incorporated herein by reference), but the crucial role of inhibitors of proliferation is demonstrated in the p27 −/− mice in this study for progenitors and in p21 −/− for stem cells elsewhere. Where there is an inability to exert the cell cycle inhibition mediated by these molecules, disruption of normal population kinetics occurs. However, the proliferation that does occur in the p21 −/− and p27 −/− mice is not as overwhelming as has been observed, for example, with disruption by an inhibitory cytokine such as TGF-β (Shull et aL "Targeted disruption of the mouse transforming growth factor-beta 1 gene results in multifocal inflammatory disease" *Nature* 359:693-699, 1992; incorporated herein by reference). Although the p27 −/− animals have slightly higher blood counts than +/+ controls (Table 8), neither the p27- nor p21-deficient animals develop leukemia or gross polycythemia as indicated by cell counts, morphology, and phenotypic analysis by flow cytometry (data not shown). Therefore, other negative regulators must be active beyond a certain threshold of cell expansion. It is within physiologic ranges of the hematopoietic compartment size that p27 and p21 appear to exert dominant roles in modulating cell dynamics.

TABLE 8

Comparison of blood cell counts indicates slightly higher leukocyte counts in p27 −/− mice (n = 10, Mean ± SD) without significant differences in other mature cell populations.

|        | WBC (× $10^3$/ul) | RBC (× $10^6$/ul) | PLT (× $10^6$/ul) |
|--------|-------------------|-------------------|-------------------|
| p27 +/+ | 6.89 ± 2.11      | 8.26 ± 1.41       | 635.40 ± 105.64   |
| p27 −/− | 9.08 ± 3.12      | 8.37 ± 1.09       | 723.10 ± 172.74   |
| p value | 0.0293           | 0.8193            | 0.0563            |

Blood was collected by tail bleeding. All the blood counts were performed and analyzed using the t-test for two samples with the same variance.

The ability of a minority population of p27 −/− stem cells to predominate in the progenitor and mature blood cell compartments indicates the potential efficacy of using p27 to enhance the efficiency of small numbers of stem cells. A controlled reduction in p27 might make it possible to effect a marked alteration in a substantially larger fraction of blood cells, particularly in the settings where small numbers of stem cells may be transduced with a therapeutic gene. The absence of untoward effect in vivo demonstrated in the p27 −/− mouse provides conceptual support. The ability of this genetic alteration to increase the size of other, non-hematopoietic tissues in vivo (Kiyokawa et al. "Enhanced growth of mice lacking the cyclin-dependent kinase inhibitor function of p27(Kip1)" *Cell* 85:721-732, 1996; Fero et al. "A syndrome of multiorgan hyperplasia with features of gigantism, tumorigenesis, and female sterility in p27 (Kip1)-deficient mice" *Cell* 85:733-744, 1996; Nakayama et al. "Mice lacking p27(Kip1) display increased body size, multiple organ hyperplasia, retinal dysplasia, and pituitary tumors" *Cell* 85:707-720, 1996; each of which is incorporated herein by reference) indicates that controlled manipulation of p27 may also be relevant for the expansion or possible regeneration of other tissue types.

Example 3

Increased Numbers of stem Cells Following ex vivo Treatment with p21 Anti-Sense

Materials and Methods

Cells and cell culture. Cells were obtained from umbilical cord blood after normal full-term deliveries, from bone marrow harvests of healthy adult volunteers and from mobilized peripheral blood of normal donors in accordance to procedures approved by the Institutional Review Board of the Massachusetts General Hospital. Samples were diluted in PBS and enriched for mononuclear cells by centrifugation on Ficoll/Paque. $CD34^+$ were enriched by immunomagnetic selection in according to the manufacturer's instructions (Miltenyi Biotec, Bergisch-Gladbach, Germany) with a purity in the selected product always of 95%. $CD34^+38^-$ cells were further enriched after staining with CD34-fluorescein isothiocyanate (FITC) and CD38-phycoerythrin (PE) (Becton Dickinson, San Jose, Calif.) by fluorescence-activated sorting (FACS Vantage, Becton Dickinson).

Human embryonic kidney derived 293T cells were grown in Dulbecco's modified Eagle's medium (DMEM) supplemented with 10% FCS, 100 U/ml penicillin, 100 U/ml sreptomycin, and 2 mM L-glutamine (GIBCO, BRL). CMK cell line was grown in RPMI supplemented with 10% FCS, 100 U/ml penicillin, 100 U/ml sreptomycin, and 2 mM L-glutamine (GIBCO, BRL).

Lentviral vectors and constructs. cDNA encoding full length $p21^{cip1}$ was subcloned as antisense into the BamHI cloning site of the lentiviral vector pHR-CMV-GFP (Miyoshi et al. *Proc. Natl. Acad. Sci. USA* 94(19):10319-10323, 1997; incorporated herein by reference). The control vector contains the cDNA encoding the green flourescent protein.

Lentviral production and transduction. The lentiviral vector containing p21cip1antisense (p21-AS-V) and the control vector (GFP-V) were cotransfected into 293T cells with pCMV encoding the gag and pol proteins, and pCMV-VSV-G, a plasmid encoding the vesicular stomatitis virus G-glycoprotein (VSV-G), using the Geneporter lipofection method in according to the manufacturer's instructions (Gene Therapy Systems, San Diego, Calif.). Supernatants containing pseudotyped lentiviruses were collected at 72 hrs after the beginning of transfection and were used for the transduction of human $CD34^+$ and $CD34^+38^-$ hematopoietic cells.

$CD34^+$ and $CD34^+38^-$ cells were cultured in Iscove's modified Dulbecco's medium (IMDM) containing 10% fetal calf serum (FCS; Sigma, St. Louis, Mo.) (IMDM 10), 100 U/ml penicillin, 100 U/ml sreptomycin and 2 mM L-glutamin (GIBCO, BRL) supplemented with stem cell factor (SCF [50 ng/ml]), Flt-3-ligand (Flt-3-L [50 ng/ml]), Thrombopoietin (TPO [25 ng/ml]) and Interleukin-3 (IL-3 [10 ng/ml]) (R&D Systems, Minneapolis, Minn.) for 24 hrs on Retronectin (Takara, Japan) coated wells. After this prestimulation, two third of the culture medium was dicarded and replaced with the viral containing supernatant plus Polybrene (final concentration 4 ,µg/ml, Sigma). The cells with the viral supernatant were spinoculated at 1700 revolutions per minute for 30 minutes, incubated at 37° C. and 5% $CO_2$ for an additional 20 hrs, than washed and plated on fresh Retronectin coated wells in IMDM 10 plus cytokines overnight. A second transduction was performed on the following day using the same procedure. Four days after beginning the transduction the transduction efficiency was measured by flow cytometric analysis (FACS Calibur, Becton Dickinson) for GFP+ cells.

Colony forming assay. Transduced CD34+ and CD34+38− cells were cultured in 0.8% methylcellulose, 30% fetal bovine serum, 1% bovine serum albumin, 0.1 mM 2-mercaptoethanol, 2 mM L-glutamine of α-MEM semi-solid matrix culture medium supplemented with cytokines (SCF [50 ng/ml], IL-3 [10 ng/ml], IL-6 [10 ng/ml] and Erythropoietin (EPO) [4 U/ml]) (StemCell Technologies Inc., Vancouver, Canada). Cells were plated at 500 cells/ml into 24-well plates and placed at 37° C. and 5% $CO_2$. At day 10, colonies were scored, totaled and reported as CFCs.

Long-term culture with limiting dilutions. To quantify the stem cells in the transduced CD34+ and CD34+38− cell population, we adapted the cobblestone area forming cell (CAFC) assay (Ploemacher et al. "An in vitro limiting-dilution assay of long-term repopulating hematopoietic stem cells in the mouse" Blood 74:2755-2763, 1989; Ploemacher et al. "Use of limiting-dilution type long-term marrow cultures in frequency analysis of marrow-repopulating and spleen colony-forming hematopoietic stem cells in the mouse" Blood 78:2527-2533, 1991; each of which is incorporated herein by reference) with minor modifications as follows. To prepare stromal layers human bone marrow nucleated cells were cultured at 33° C. in long-term culture (LTC) medium (α-MEM with 12.5% horse serum, 12.5% fetal bovine serum, 0.2 mM I-inositol, 20 mM folic acid, 0.1 mM M 2-mercaptoethanol, 2 mM L-glutamine, and 1 µM hydrocortisone; StemCell Technologies). After 4-8 weeks the confluent stromal layers were trypsinized, irradiated (15 Gy), and subcultured in 96-well plates at a density of $2.5 \times 10^4$ cells per well. The transduced CD34+ and CD34+38− cells were then seeded with 2-fold diluted single cell suspensions in the same LTC-medium. Half of the medium was replaced weekly and the CAFC's were scored until the 6th week (Ploemacher et al. "Use of limiting-dilution type long-term marrow cultures in frequency analysis of marrow-repopulating and spleen colony-forming hematopoietic stem cells in the mouse" Blood 78:2527-2533, 1991; incorporated herein by reference). To measure LTC-initiating cells (LTC-IC) the semisolid, cytokine containing methylcellulose medium for CFC (s.a.) was overlaid into the wells at week 5 and the colonies were counted at day 10. A limiting dilution analysis software program (Maxrob, kindly provided by Julian Down, BioTransplant Inc.) was used to calculate the frequency of LTC-ICs in the cell population.

Liquid culture. To examine the affect of p21-antisense on the differentiation and expansion of hematopoietic cells transduced CD34+ and CD34+38− cord blood cells were cultured in IMDM 10 supplemented with SCF [50 ng/ml], Flt-3 [50 ng/ml] and TPO [10 ng/ml]. Weekly the medium was replaced and half of the cells were taken for further analysis. To measure the proportion of primitive cells in the liquid culture, cells were stained with CD34-PerCP and CD38-APC (Becton Dickinson), incubated with propidium iodid to distinguish between viable and dead cells, and analyzed by flow cytometry.

NOD/SCID repopulation assay. To evaluate the repopulation ability of the transduced human CD34+ cells we used a NOD/SCID repopulation assay. NOD/SCID mice (Jackson Laboratories, Bar Harbor, Me.) were handled under sterile conditions and maintained under mircoisolaters. Transduced CD34+ umbilical cord blood cells were transplanted by tail vein injection into sublethal irradiated (3.5 Gy) 8-week-old mice along with $1.5 \times 10^6$ irradiated (20 Gy) nonrepopulating human bone marrow mononuclear cells. Every two weeks after the first month ca. 200 µl of peripheral blood was obtained from each recipient mice by tail bleeds. The blood was stained with CD45-PerCP, CD38-APC (Becton Dickinson) antibodies, treated with a lysis buffer (ACK Lysis buffer), incubated with propodium iodid to distinguish between viable and dead cells, and analyzed by flow cytometry to detect human derived hematopoietic progenitors (FACS-Calibur, Becton Dickinson). Mice were sacrificed 6 to 12 weeks after transplantation. Bone marrow from femurs and tibiae of each mouse were flushed into IMDM containing 10% FCS and analyzed by flow cytometry (FACS-Calibur, Becton Dickinson).

Flow cytometric analysis. Flow cytometry was used to estimate the transduction efficiency and content of stem cells in the transduced cell population 4 days after the beginning of the transduction. Cells were stained with CD34-PerCP and CD38-APC (Becton Dickinson) and incubated with propidium iodid shortly prior to the flow cytometric analyis, to distinguish between viable and dead cells.

To quantify the repopulation ability of the transplanted transduced CD34+ cord blood cells in the peripheral blood and the bone marrow of the tranplanted animals (NOD/SCID repopulation assay s.a.) bone marrow nucleated cells were labeled with the human leukocyte antibody CD45-PerCP, stem cell markers (CD34-PE and CD38 APC), and lineage antibodies (CD3-APC, CD11-APC, CD14-APC, CD19-APC (Becton Dickinson), CD41 PE and Glycophorin A. The viability of the stained cells were measured by staining with propidium iodid (PI) or 7-AAD 15 min prio to the analysis and gating on PI or 7-AAD negative cells. The stained cell samples were analyzed on a FACScalibur cytometer (Becton Dickinson).

Flow cytometric analysis of the cell cycle status. Transduced CD34+ cord blood cells were stained with CD34-PE and CD38-APC (Becton Dickinson) followed by an incubation with a DNA-dye Hoechst33342 (Hst, 1.67 µmol/l) (Hoechst) and RNA-dye, PyroninY (PY, 1 ,µg/ml) (Gothot et al. "Functional heterogeneity of human CD34(+) cells isolated in subcompartments of the G0/G1 phase of the cell cycle" Blood 90:4384-4393, 1997; incorporated herein by reference). The proportion of cells in $G_0$ as $PY^{low}$ $Hoechst^{low}$ cells was measured in the CD34+38− cell subpopulation, representing quiescent primitive hematopoietic cells.

Western blot analysis. To confirm that transduction of the p21-AS-V leads to an decreased expression of p21, CMK cells ($2 \times 10^6$) were transduced with p21-AS-V and the control vector followed by a stimulation with TPA (100 nM, Sigma) 24 hrs after the beginning of transduction to induce p21-expression. After further 24 hours cells were lysed in an ELB lysing buffer. Total protein was separated in 12.5% denaturating gel, blotted on a membrane and probed with anti-human p21 (clone 6B6, Pharmingen, San Diego, Cailf.).

Statistical analysis. The significance of the difference between groups in the in vitro and in vivo experiments were evaluated by analysis of variance followed by a two-tailed Student's t-test.

Results

Lentiviral expression of p21-antisense in human CD34+ cord blood cells. cDNA encoding full length $p21^{cip1}$ was subcloned into pHR'-CMV-GFP (GFP-V), a lentiviral vector that allows coexpression of subdloned cDNAs and green fluorescent protein (GFP) from a single MRNA transcript (Miyoshi et al. Proc. Natl. Acad. Sci. USA 94(19):10319-10323, 1997; incorporated herein by reference), as antisense (p21 -AS-V).

Figure 11B:
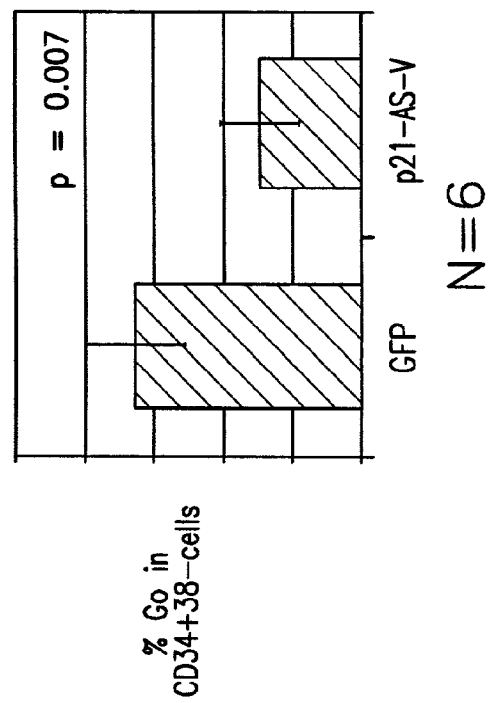
FIG. 11. p21-antisense reduces the $G_0$ fraction of transduced CD34$^+$ cord blood cells. In six independent experiments, transduction of p21-antisense decreased the proportion of cells in $G_0$ in the CD34$^+$38$^-$ subpopulation of transduced CD34$^+$ cordblood cells (7.3% p21-AS-V vs. 16.4% GFP-V; p=0.007.
Figure 11A:
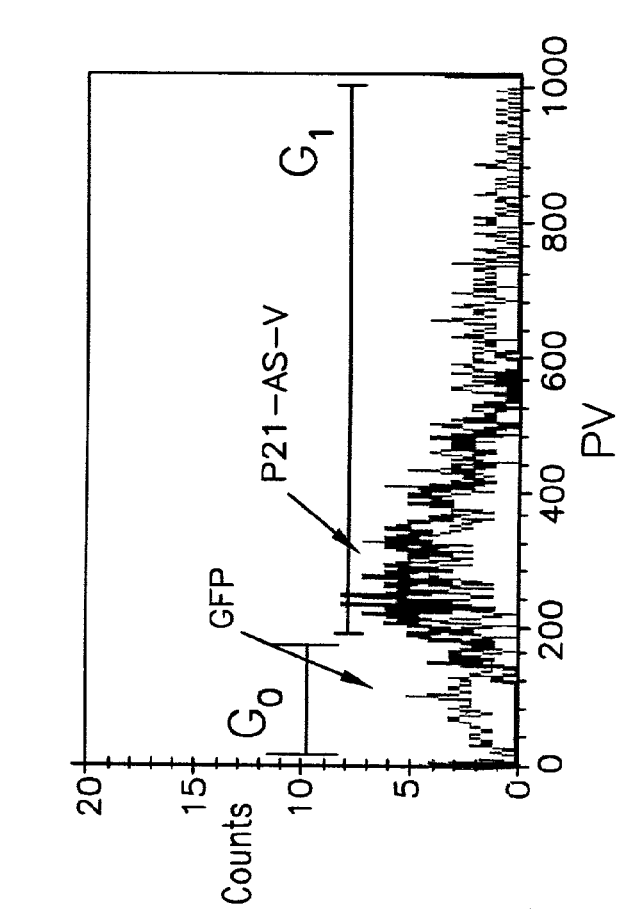
Figure 12A:
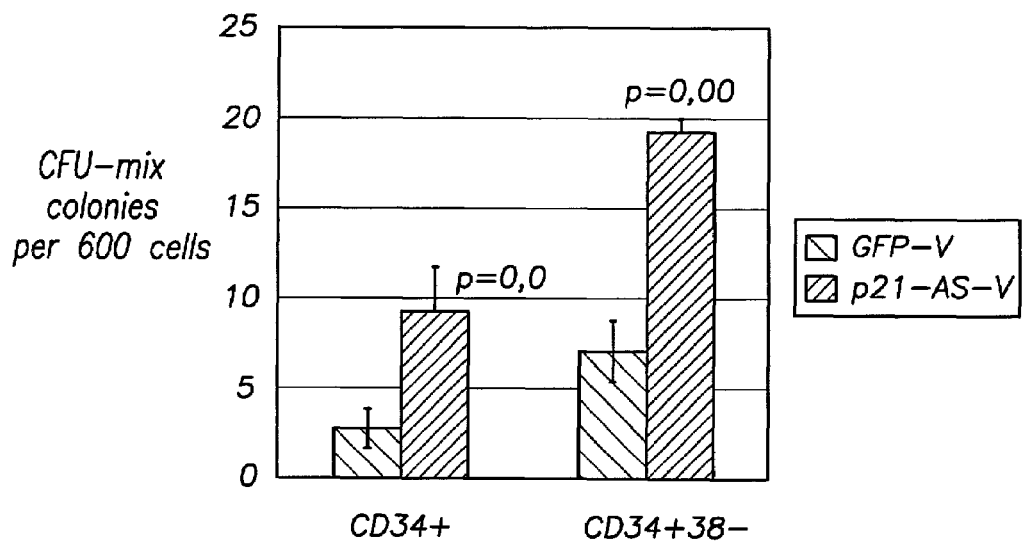
FIG. 12. Antisense-p21 increases primitive CFU-mix without altering total CFC in transduced CD34$^+$ and CD34$^+$38$^-$ cord blood cells. (a) The colonies generated by cells expressing p21 -antisense showed a higher proportion of colonies with myeloid and erythroid cells (CFU-mix) representing more primitive hematopoietic cells than colonies of the control vector transduced cells (CD34$^+$: 9.3 vs. 2.8 colonies/600 cells, p=0.02; CD34$^+$38$^-$: 19.2 vs. 7.1 colonies/600 cells, p-0.002). (b) Transduced cells were plated four days after the beginning of transduction in semisolid CFC-medium. Neither CD34$^+$ (n=4) nor CD34$^+$38$^-$ cells transduced with p21 -antisense showed an altered total colony number compared to cells transduced with the control vector.
Figure 12B:
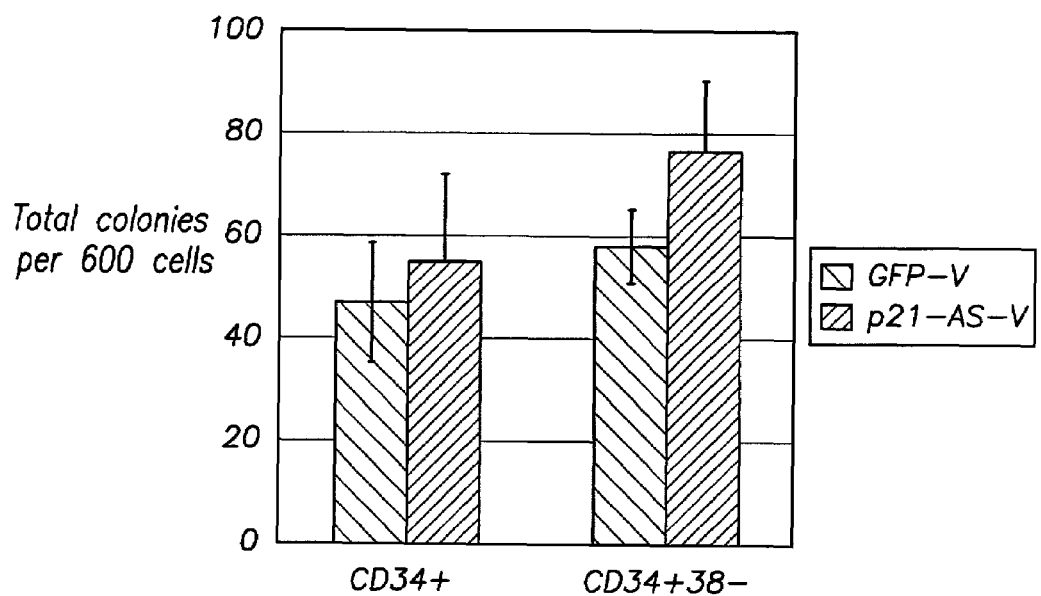

The transduction efficiency of human CD34+ and CD34+ 38- cord blood cells by p21-AS-V was measured by flow cytometric analysis. Independent experiments showed a transduction efficiency of 45-55% for the control vector (GFP-V) and 25-35% for the p21-AS-V lentiviruses four days after the beginning of transduction. At this time point cells were used for in vitro and in vivo experiments.

p21-antisense reduces the $G_0$ fraction of transduced CD34$^+$ cord blood cells. To evaluate the ability of p21-antisense to alter cell cycle kinetics we analyzed the cell cycle status of transduced CD34$^+$ cord blood cells by simultaneously staining with DNA and RNA dyes, which allows the distinction between cells in $G_0$ and $G_1$ (Gothot et al. "Functional heterogeneity of human CD34(+) cells isolated in subcompartments of the G0/G1 phase of the cell cycle" Blood 90:4384-4393, 1997; Cheng et al. "Hematopoietic stem cell quiescence maintained by p21 (cip1/waf1)" Science 287:1804-1808, 2000; each of which is incorporated herein by reference). Cells determined to be in the $G_0/G_1$ phase of the cell cycle based on the Hst fluorescence distribution can be further fractionated into subcompartments of varying cellular RNA content by staining with PY. Quiescent cells, in $G_0$, have a low RNA content. As cells progress through $G_1$, they accumulate RNA and finally move to the S/$G_2$+M phase during which Hst staining increases. In 6 independent experiments transduction of p21-antisense decreased the proportion of cells in $G_0$ in the CD34$^+$38$^-$ subpopulation of transduced CD34$^+$ cord-blood cells (7.3% p21-AS-V vs. 16.4% GFP-V; p=0.007), indicating that p21-antisense promotes the entry of quiescent cells into the cell cycle (FIG. 11). p21-antisense increases primitive hematopoietic cells in transduced CD34$^+$ and CD34$^+$38$^-$ cord blood cells in vitro. We next sought to define the impact of p21-antisense on the differentiation status of transduced CD34$^+$ and CD34$^+$38$^-$ cord blood cells in vitro. Transduced cells were analyzed for their ability to generate colonies using methylcellulose colony forming (CFC) assays for progenitor function. Transduced cells were plated four days after the beginning of transduction in semisolid CFC-medium. Neither CD34$^+$(n=4) nor CD34$^+$38$^-$ cells transduced with p21-antisense showed a altered total colony number compared to cells transduced with the control vector (FIG. 12B). Of note, however, the colonies generated by cells expressing p21-antisense showed a higher proportion of colonies with myloid and erythroid cells (CFU-mix) representing more primitive hematopoietic cells than colonies of the control vector transduced cells (CD34$^+$: 9.3 vs. 2.8 colonies/600 cells, p=0.02; CD34$^+$38$^-$: 19.2 vs. 7.1 colonies/600 cells, p=0.002) (FIG. 12A).

Figure 13:
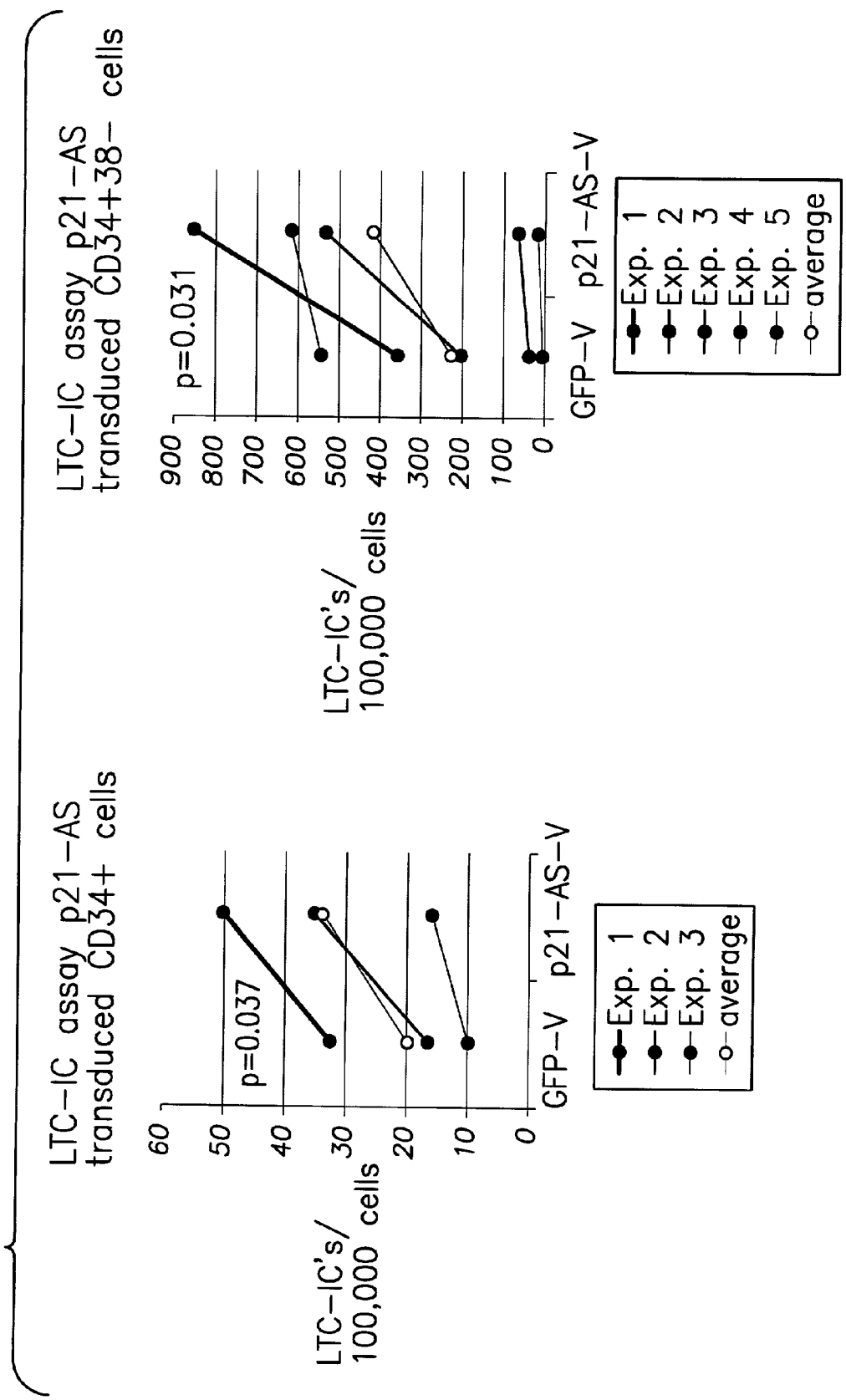
FIG. 13. Antisense-p21 expands LTC-IC as assessed by limiting dilution analysis. CD34$^+$ and CD34$^+$38$^-$ cells transduced with p21-antisense gave rise to a significantly higher number of long-term culture initiating cells (LTC-ICs) compared with cells transduced with the control vector, indicating a higher proportion of stem cells in the p21 -antisense transduced cell population (CD34$^+$: 33.5 vs. 19.3 LTC-ICs/100000 cells (p=0.04); CD34$^+$38$^-$: 416 vs. 228 LTC-ICs/100000 cell (p=0.03))
Figure 14:
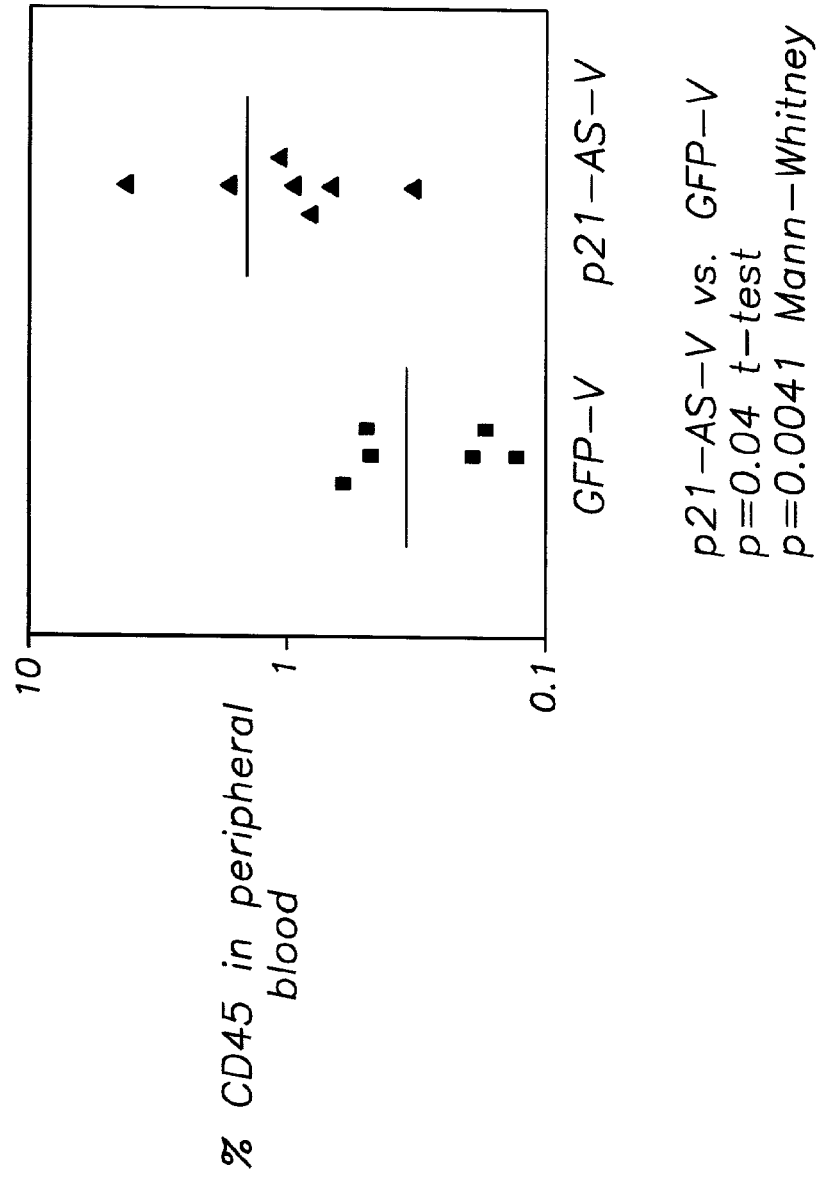
FIG. 14. p21$^{cip1}$ anti-sense enhances human CD34$^+$ cell engraftment of NOD/SCID mice.

To quantify the stem cell frequency in the transduced CD34$^+$ and CD34$^+$38$^-$ cell population, we performed long-term cultures with limiting dilutions on primary human bone marrow stroma (LTC-IC-assay). CD34$^+$ and CD34$^+$38$^-$ cells transduced with p21-antisense gave rise to a significantly higher number of long-term culture initiating cells (LTC-ICs) compared with cells transduced with the control vector, indicating a higher proportion of stem cells in the p21-antisense transduced cell population (FIG. 13, CD34$^+$: 33.5 vs. 19.3 LTC-ICs/100000 cells (p=0.04); CD34$^+$38$^-$: 416 vs. 228 LTC-ICs/100000 cells (p =0.03)). Like in the CFC-assay overexpression of p21-antisense led to an increase of primitive hematopoietic cells in comparison to control vector transduced cells. Thus, p21-antisense expands or preserves primitive hematopoietic cells measured by functional in vitro assays.

p21-antisense increases stem cell numbers as measured by repopulation of NOD/SCID mice. The ability of human cells to engraft multiply immunodeficient, NOD/SCID, mice has provided an in vivo model of a stem cell functional phenotype. The abundance of human cells in the blood or bone marrow of engrafted animals correlates with the input number of stem cells. Using this assay, we transplanted human cells transduced with either control vector or the p21-antisense vector into irradiated mice and evaluated human cell engraftment. Cells transduced with control vector demonstrated minimal engraftment, substantially different from those transduced with the p21-antisense vector. Therefore, p21-antisense enhances the number of stem cells as measured by this in vivo model of stem cell function. FIG. 14 demonstrates the percent of human cells detectable in the blood of animals transplanted with cells exposed to either control (GFP-V) or p21-anti-sense encoding (p21-AS-V) vector.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. method of expanding a population of hematopoietic stem cells, the method comprising steps of:
   providing at least one hematopoietic stem cell with less than wild type p21 activity and a lack of inhibition of p27 activity; and
   expanding the cell population.

2. The method of claim 1, wherein the step of providing comprises:
   providing a hematopoietic stem cell; and
   disrupting the cell's p21 gene.

3. The method of claim 1, wherein the step of providing comprises:
   providing a hematopoietic stem cell; and
   contacting the cell with an agent, wherein the agent inhibits p21 activity.

4. The method of claim 1, wherein the cell is an erythropoietic cell.

5. The method of claim 1, wherein the cell is a granulopoietic cell.

6. The method of claim 1, wherein the cell is a thrombopoietic cell.

7. The method of claim 1, wherein the cell is an adult-derived hematopoietic stem cell.

8. The method of claim 1, wherein the cell is an embryonically derived hematopoietic stem cell.

9. The method of claim 1, wherein the cell is a multi-potential hematopoietic stem cell.

10. The method of claim 1, wherein the cell is a fetal cell.

11. The method of claim 1, wherein the cell is an embryonic cell.

12. The method of claim 3, wherein the agent is a protein.

13. The method of claim 3, wherein the agent is a peptide.

14. The method of claim 3, wherein the agent is a polynucleotide.

15. The method of claim 3, wherein the agent is a chemical compound.

16. The method of claim 3, wherein the agent is an antibody or fragment thereof.

17. The method of claim 3, wherein the agent is an antisense agent.

18. The method of claim 3, wherein the agent is a triple helix forming agent.

19. The method of claim 3, wherein the agent is an aptamer.

20. An isolated hematopoietic stem cell with less than wild type p21 activity and a lack of inhibition of p27 activity.

21. The stem cell of claim 20 with at least one copy of the p21 gene disrupted.

22. The stem cell of claim 20 with both copies of the p21 gene disrupted.

23. The method of claim 3, wherein the agent is an RNA inhibiting agent.

* * * * *